United States Patent [19]
Seilhamer et al.

[11] Patent Number: 6,023,659
[45] Date of Patent: Feb. 8, 2000

[54] DATABASE SYSTEM EMPLOYING PROTEIN FUNCTION HIERARCHIES FOR VIEWING BIOMOLECULAR SEQUENCE DATA

[75] Inventors: Jeffrey J. Seilhamer, Los Altos Hills; Ingrid E. Akerblom, Redwood City; Christina M. Altus; Tod M. Klingler, both of Palo Alto; Frank Russo, Redwood City; Janice Au-Young, Berkeley; Jennifer L. Hillman, Mt. View; Timothy J. Maslyn, Cupertino, all of Calif.

[73] Assignee: Incyte Pharmaceuticals, Inc., Palo Alto, Calif.

[21] Appl. No.: 08/812,290

[22] Filed: Mar. 6, 1997

Related U.S. Application Data

[60] Provisional application No. 60/032,563, Dec. 12, 1996, and provisional application No. 60/028,284, Oct. 10, 1996.

[51] Int. Cl.$^7$ .................................................. G06F 7/08
[52] U.S. Cl. ................................ 702/19; 702/20; 702/31
[58] Field of Search ........................... 364/496, 498; 395/606; 435/6; 702/19, 20, 27, 31, 32, 3, 7, 100, 205

[56] References Cited

U.S. PATENT DOCUMENTS

| | | | |
|---|---|---|---|
| 5,418,944 | 5/1995 | DiPace et al. | 702/27 |
| 5,523,208 | 6/1996 | Kohler et al. | 435/6 |
| 5,706,498 | 1/1998 | Fujimiya et al. | 395/606 |

OTHER PUBLICATIONS

The Institute for Genomic Research, TIGR Database. Internet—http://www.tigr.org (Downloaded Dec. 23, 1997).
National Center for Biotechnology Information (Index). Internet—http://www3.ncbi.nlm.nih.gov/ (Downloaded Dec. 23, 1997).
National Center for Biotechnology Information; ENTREZ. Internet—http://www3.ncbi.nlm.nih.gov/entrez (Downloaded Dec. 23, 1997).
National Center for Biotechnology Information; UniGene. Internet—http://www3.ncbi.nlm.nih.gov/unigene (Downloaded Dec. 23, 1997).
National Center for Biotechnology Information; GenBank. Internet—http://www3.ncbi.nlm.nih.gov/web/genbank (Downloaded Dec. 23, 1997).
MAGPIE; Automated Genome Project Investigation Environment. Internet—http://www.mcs.anl.gov/home/gaasterl/magpie.html (Downloaded Dec. 23, 1997).
Stanford University, Stanford Genomic Resources. Internet—http://genome-www.stanford.edu.
Incyte Pharmaceuticals, LIFESEQ Version 4.2 Release Notes and Physical Data Model, Oct. 1996.
Incyte Pharmaceuticals, LIFESEQ Version 4.1 Release Notes and Physical Data Model, Jul. 1996.
Incyte Pharmaceuticals, LIFESEQ Version 3.4 Release Notes, Jan. 1996.

(List continued on next page.)

*Primary Examiner*—Melanie A. Kemper
*Attorney, Agent, or Firm*—Beyer & Weaver, LLP

[57] ABSTRACT

Disclosed is a relational database system for storing biomolecular sequence information in a manner that allows sequences to be catalogued and searched according to one or more protein function hierarchies. The hierarchies allow searches for sequences based upon a protein's biological function or molecular function. Also disclosed is a mechanism for automatically grouping new sequences into protein function hierarchies. This mechanism uses descriptive information obtained from "external hits" which are matches of stored sequences against gene sequences stored in an external database such as GenBank. The descriptive information provided with the external database is evaluated according to a specific algorithm and used to automatically group the external hits (or the sequences associated with the hits) in the categories. Ultimately, the biomolecular sequences stored in databases of this invention are provided with both descriptive information from the external hit and category information from a relevant hierarchy or hierarchies.

45 Claims, 18 Drawing Sheets

OTHER PUBLICATIONS

Incyte Pharmaceuticals, LIFESEQ Version 2.5 Release Notes, Jun. 1995.

Incyte Pharmaceuticals, LIFESEQ Version 3.0 Release Notes, Sep. 1995.

Incyte Pharmaceuticals, LIFESEQ Version 4.0 Release Notes, Apr. 1996.

Incyte Pharmaceuticals, *Introduction to the LIFESEQ Database, Version 3.4,* Jan. 1996.

Incyte Pharmaceuticals, *LIFESEQ Training Manual,* Version 4.1, Jul. 1996.

Green et al., "Ancient Conserved Regions in New Gene Sequences and the Protein Databases" Science, v. 259, n. 5102, pp. 1711–1716, Mar. 19, 1993.

http://wehih.wehi.edu.au/, Dec. 12, 1995.

Waldrop, "On–line Archives Let Biologists Interrogate the Genome", Science, v. 269 n. 5229, pp. 1356–1358, Sep. 8, 1995.

No Author, "Incyte Serves Up Information, part I", In Vivo the Business & Medicine Report, p. 32 ISSN: 0258–851X, May 1996.

Martin et al., "Accessing Genetics Databases" Database, v. 17, n.1, p. 51(8), Feb. 1994.

SWISS–PROT, *Enzyme: Enzyme nomenclature database.* Internet—http://expasy.hcuge.ch/sprot/enzyme.html (Downloaded Feb. 28, 1997).

*EcoCyc: Electronic Encyclopedia of E.coli Genes and Metabolism.* Internet—http://www.ai.sri.com/ecocyc/ ecocyc.html (Downloaded Feb. 28, 1997).

*Taxonomy of Genes* (EcoCyc). Internet—http://www.ai.sri.com:1555/class–subs?object=Genes (Downloaded Mar. 19, 1997).

*GenProtEC: E. coli genome and proteome database.* Internet—http://www.mbl.edu/html/ecoli.html (Downloaded Feb. 28, 1997).

Keele, J.W., "A Conceptual Database Model for Genomic Research," *Journal of Computational Biology,* vol. 1, No. 1, pp. 65–76, (1994).

Fickett, J.W., "Finding Genes by Computer: the State of the Art," *TIG* vol. 12, No. 8, pp. 316–320 (1996).

"GDB 6.0 Goals," http://gdb.gdbnet.ad.jp/gdb/docs/gdb6–goals.htm, pp. 1–5 (1995).

Matsubara, K. and Okubo, K. "Identification of New Genes by Systematic Analysis of cDNAs and Database Construction", Current Opinion in Biotechnology, 1993, No. 4, pp. 672–677.

Kanehisa, M. "Toward Pathway Engineering: A New Database Old Genetic and Molecular Pathways." Science and Technology Japan, 1995, No. 59, pp. 34–38.

Gaasterland, T. and Sensen, C. "Using Multiple Tools for Automated Genome Interpretation in an Integrated Environment", Trends In Genetics, Jan. 1996.

Adams, M.D. et al. "Complementary DNA Sequencing: Expressed Sequence Tags and Human Genome Project", Science, Jun. 21, 1991, vol. 252, pp. 1651–1656.

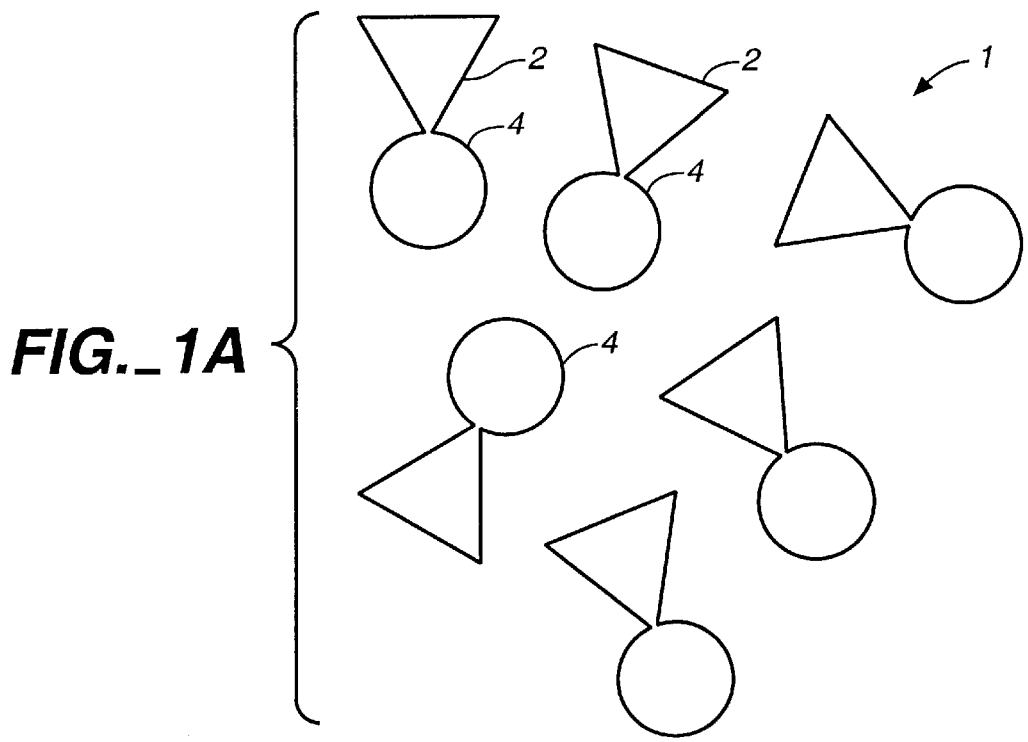
FIG._1A
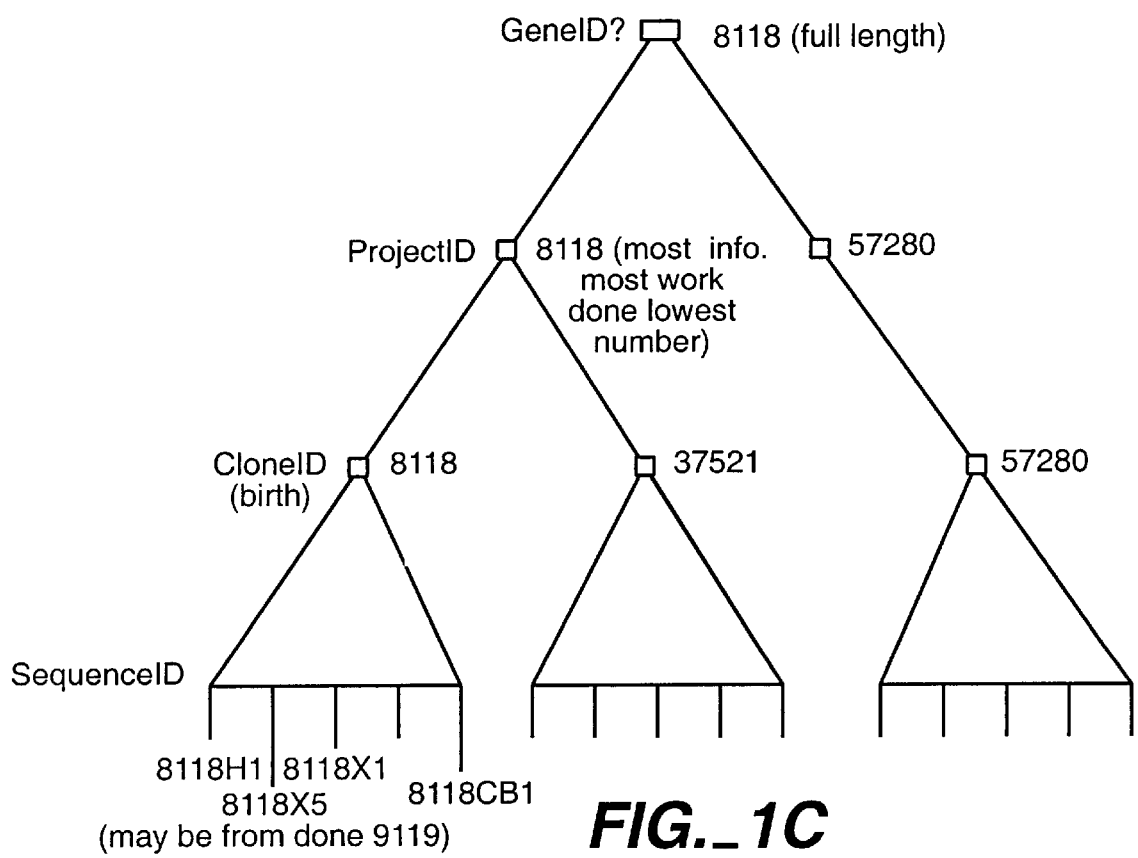
FIG._1C

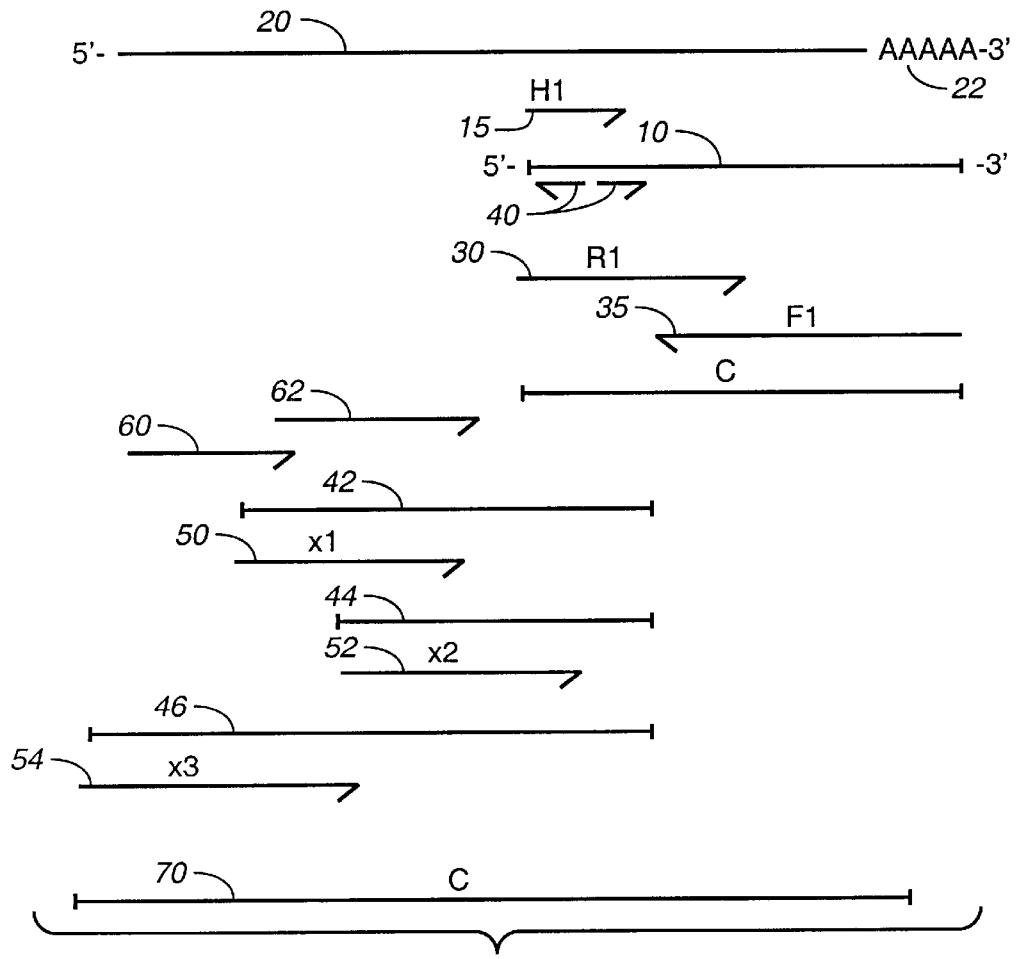
FIG._1B
FIG._1D

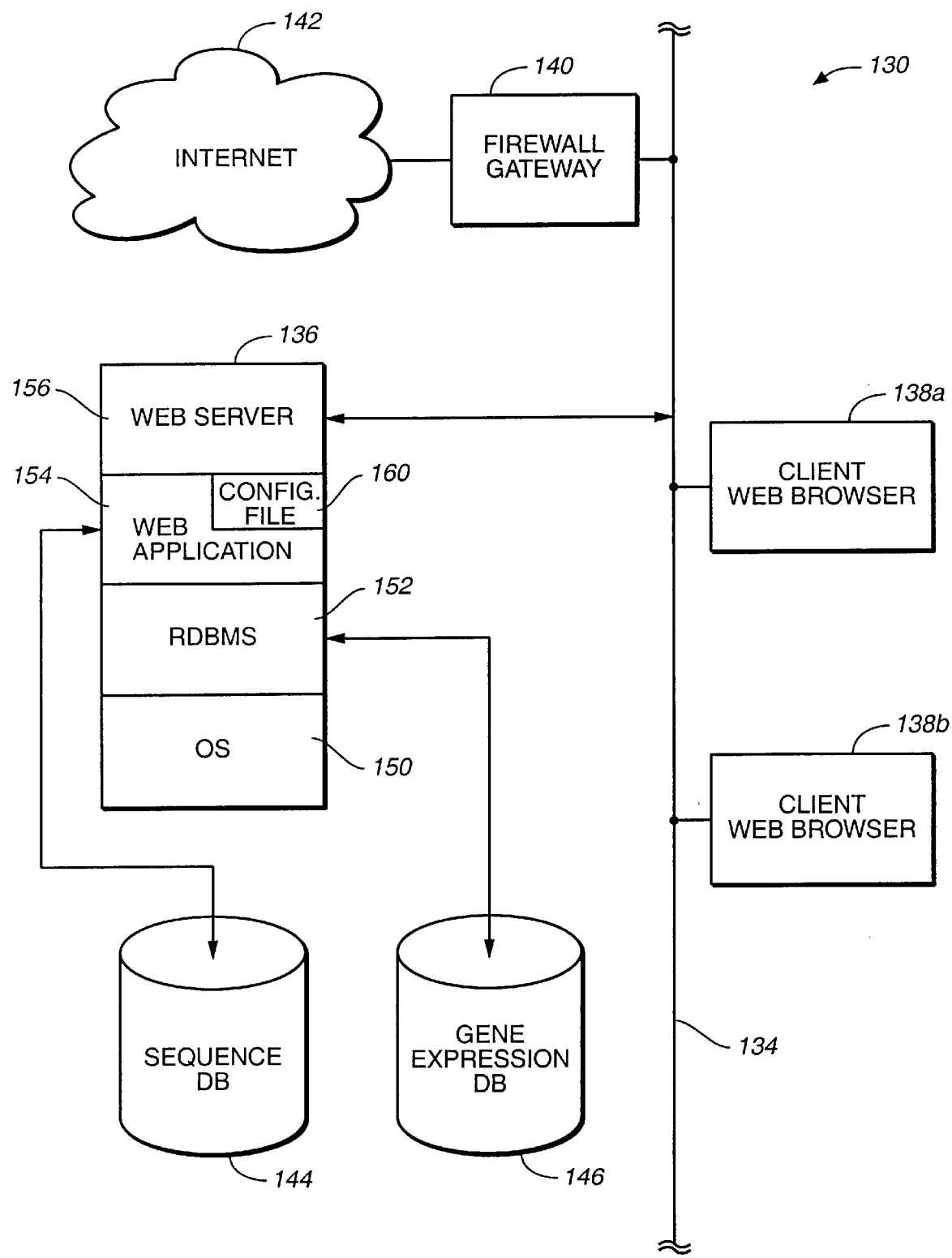
FIG._2A

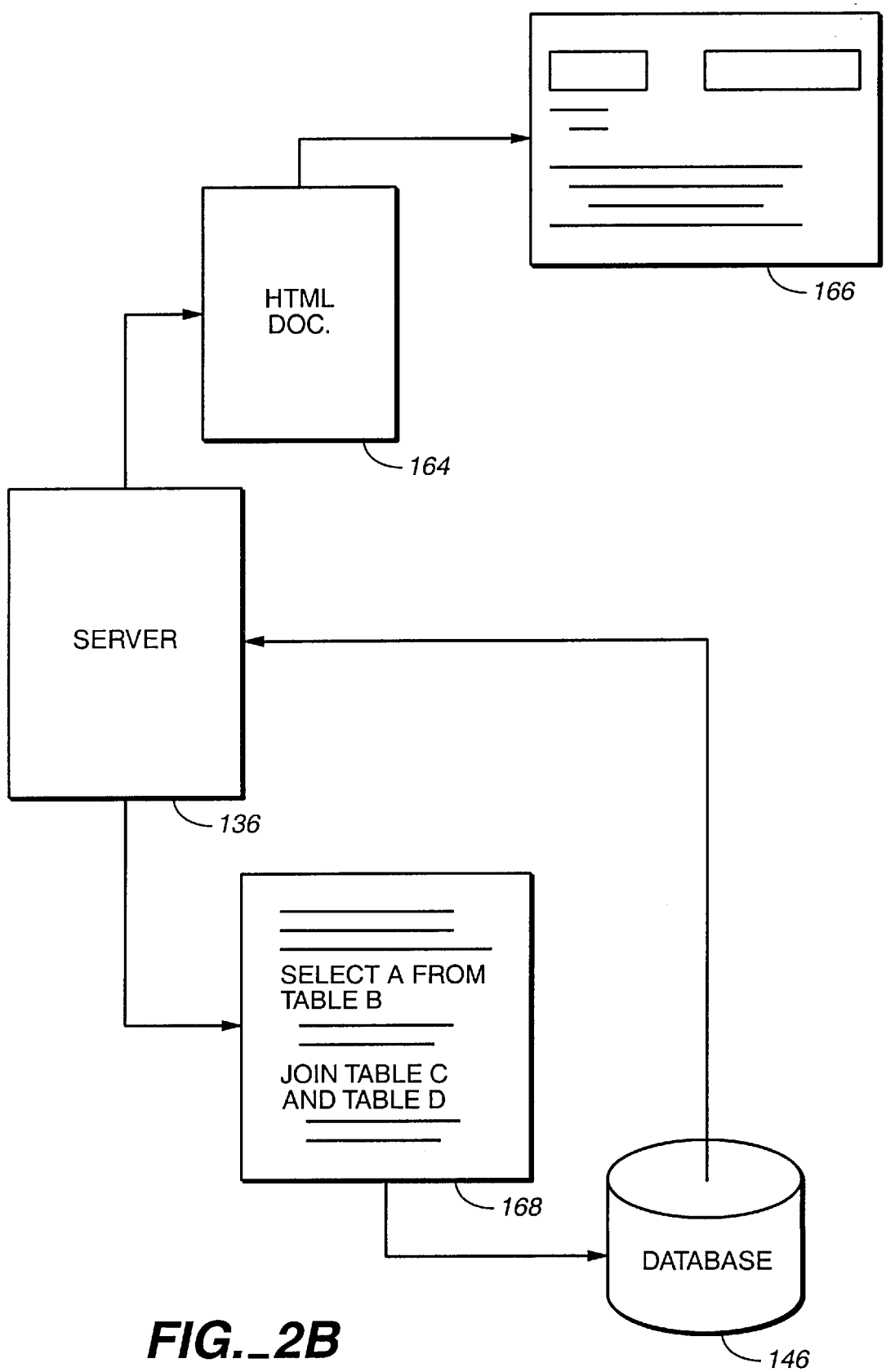
FIG._2B

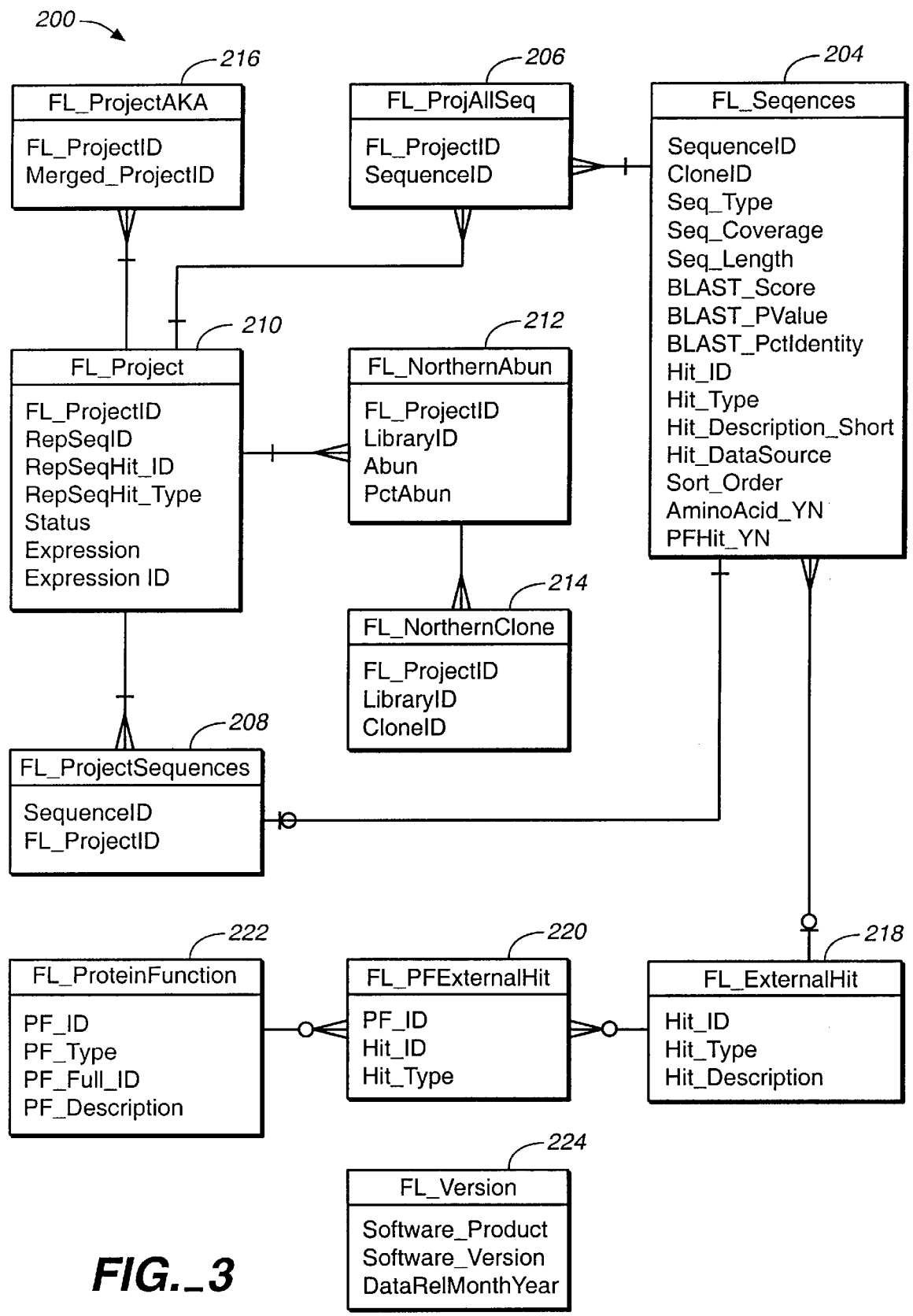
FIG._3

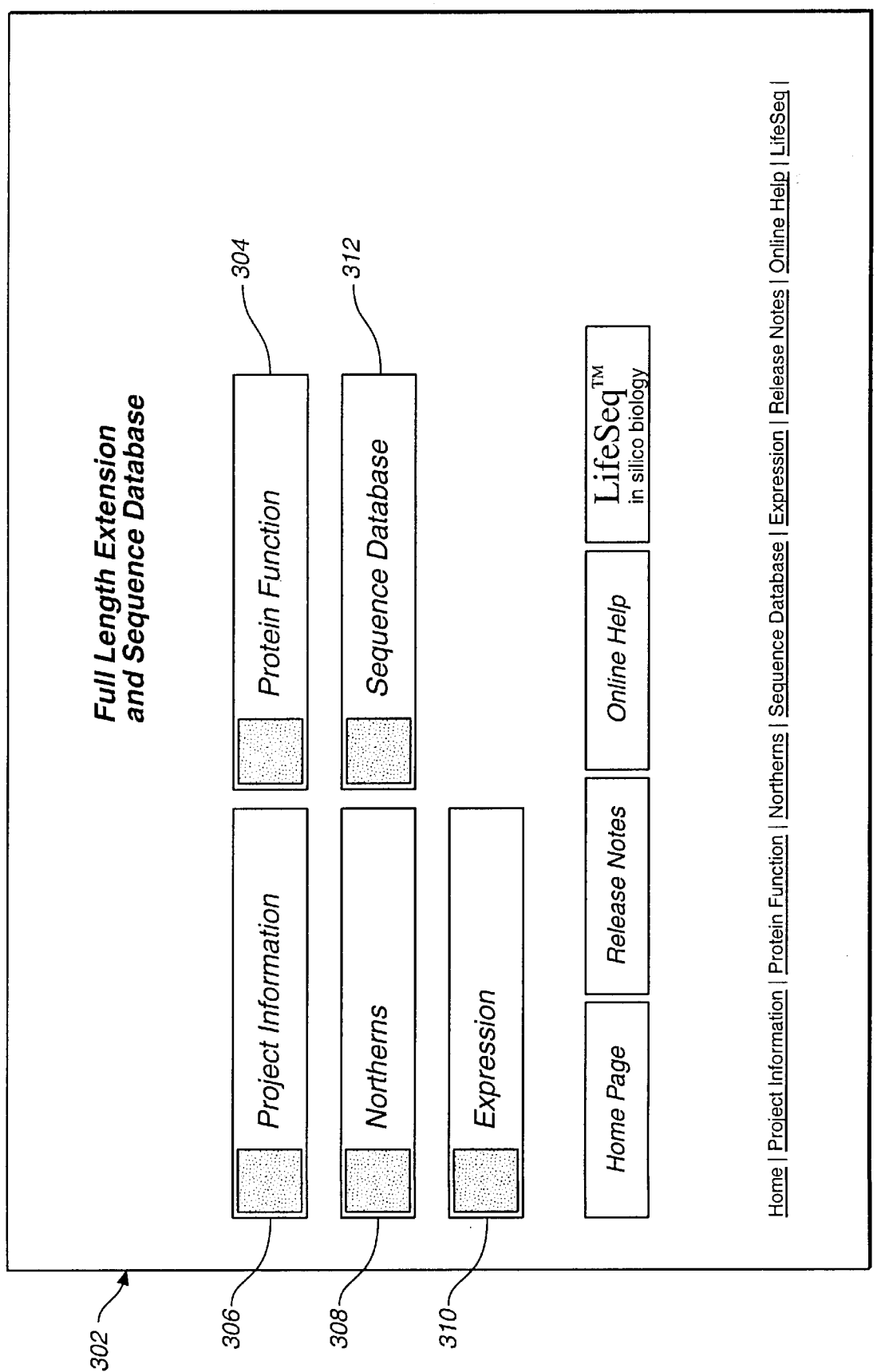
FIG._4A

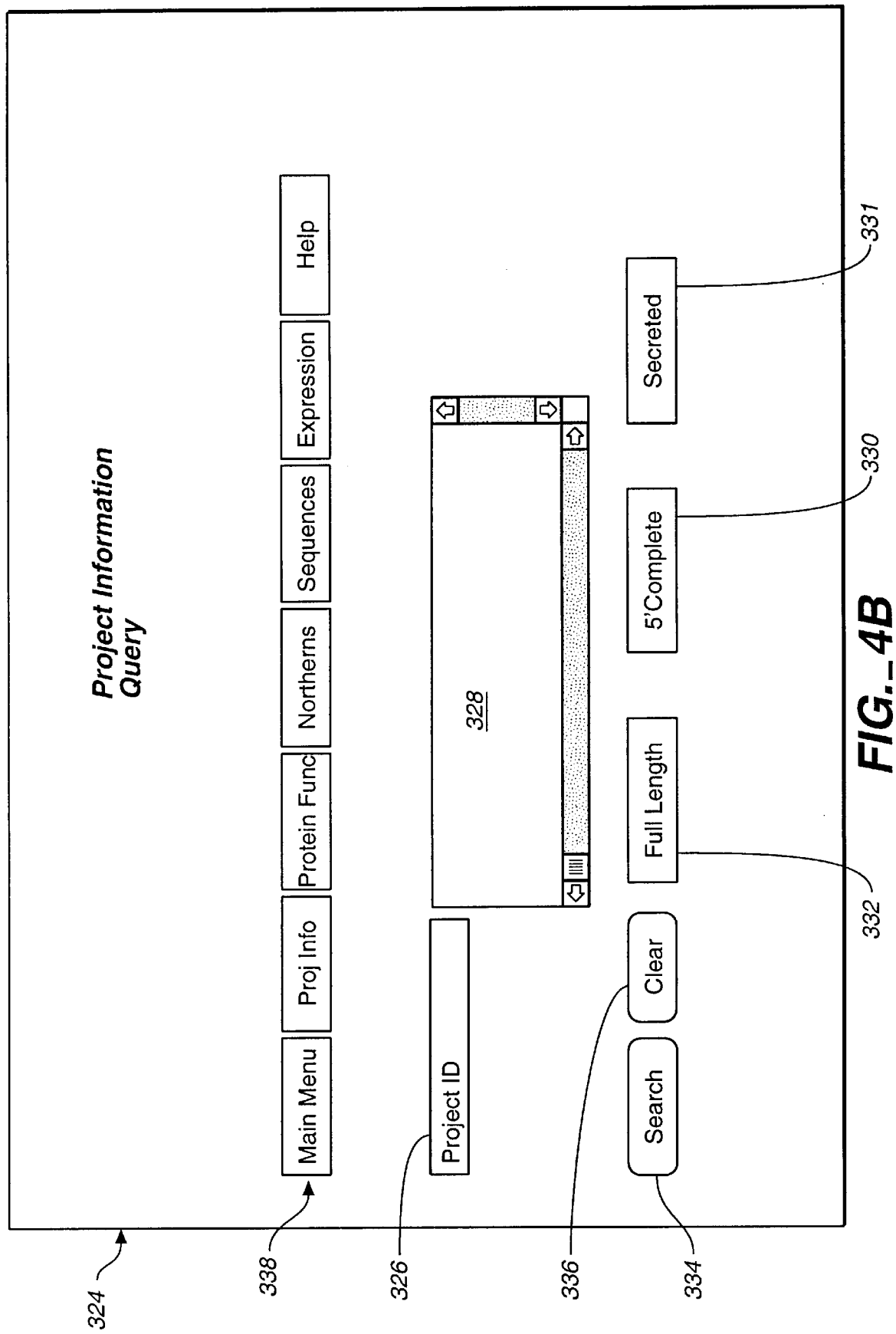
FIG._4B

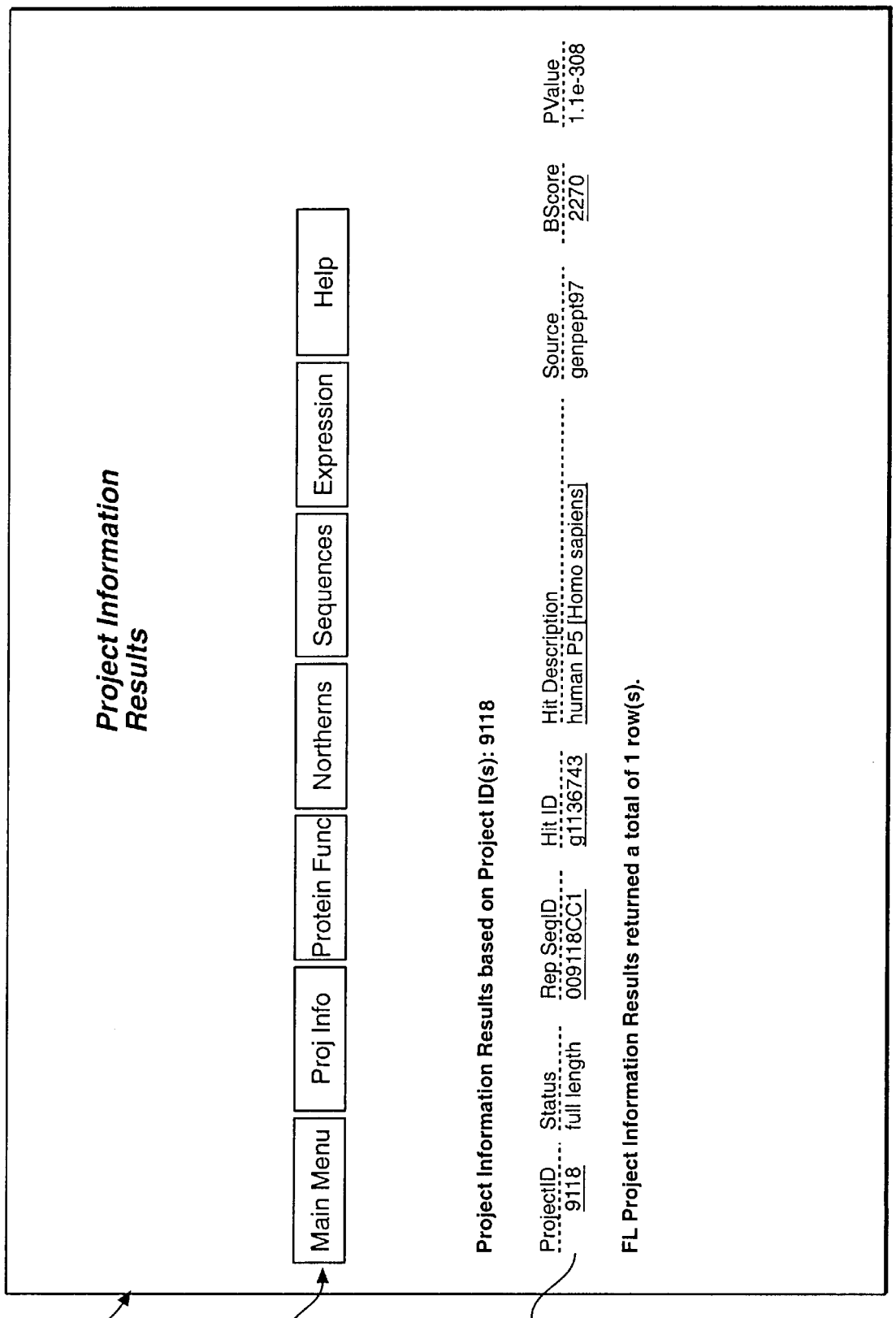
FIG._4C

Sequence Information Results

Sequence Information Results based on project ID(s):
9118
for sequences clustered with the projects(s)

| Asn | SequenceID | Sequence Type | ProjectID | HitID | Hit Description | 5' Coverage | Source | Score | PValue |
|---|---|---|---|---|---|---|---|---|---|
| ☒ | 009118CC1 | Full length | 9118 | gi1136743 | human P5 [Homo sapiens] | | genpept97 | 2270 | 1.1e-308 |
| ☒ | 009118F1 | HTP forward long read | 9118 | gi1136743 | human P5 [Homo sapiens] | | genpept97 | 732 | 1.3e-127 |
| ☒ | 009118X3 | HTP extension | 9118 | gi1136743 | human P5 [Homo sapiens] | | genpept97 | 691 | 1.4e-108 |
| ☒ | 009118H1 | HTP first pass | 9118 | gi1136743 | human P5 [Homo sapiens] | | genpept97 | 469 | 1.4e-61 |
| ☒ | 011255H1 | HTP first pass | 9118 | gi1136742 | Human mRNA for protein disulfide isomera | | gb97pri | 827 | 9.4e-98 |
| ☒ | 030811H1 | HTP first pass | 9118 | gi1136742 | Human mRNA for protein disulfide isomera | | gb97pri | 1361 | 3.7e-107 |
| ☒ | 031754H1 | HTP first pass | 9118 | gi1136742 | Human mRNA for protein disulfide isomera | | gb97pri | 1337 | 7.9e-103 |
| ☒ | 032811H1 | HTP first pass | 9118 | gi1136742 | Human mRNA for protein disulfide isomera | | gb97pri | 1327 | 4.5e-106 |
| ☒ | 034208H1 | HTP first pass | 9118 | gi1136742 | Human mRNA for protein disulfide isomera | | gb97pri | 1462 | 3.0e-113 |
| ☒ | 043333H1 | HTP first pass | 9118 | gi1136742 | Human mRNA for protein disulfide isomera | | gb97pri | 1274 | 1.4e-97 |
| ☒ | 043866H1 | HTP first pass | 9118 | gi1136742 | Human mRNA for protein disulfide isomera | | gb97pri | 1468 | 9.4e-114 |
| ☒ | 045238H1 | HTP first pass | 9118 | gi1136742 | Human mRNA for protein disulfide isomera | | gb97pri | 975 | 2.8e-94 |

[Main Menu] [Proj Info] [Protein Func] [Northerns] [Sequences] [Expression] [Help]

FIG._4D

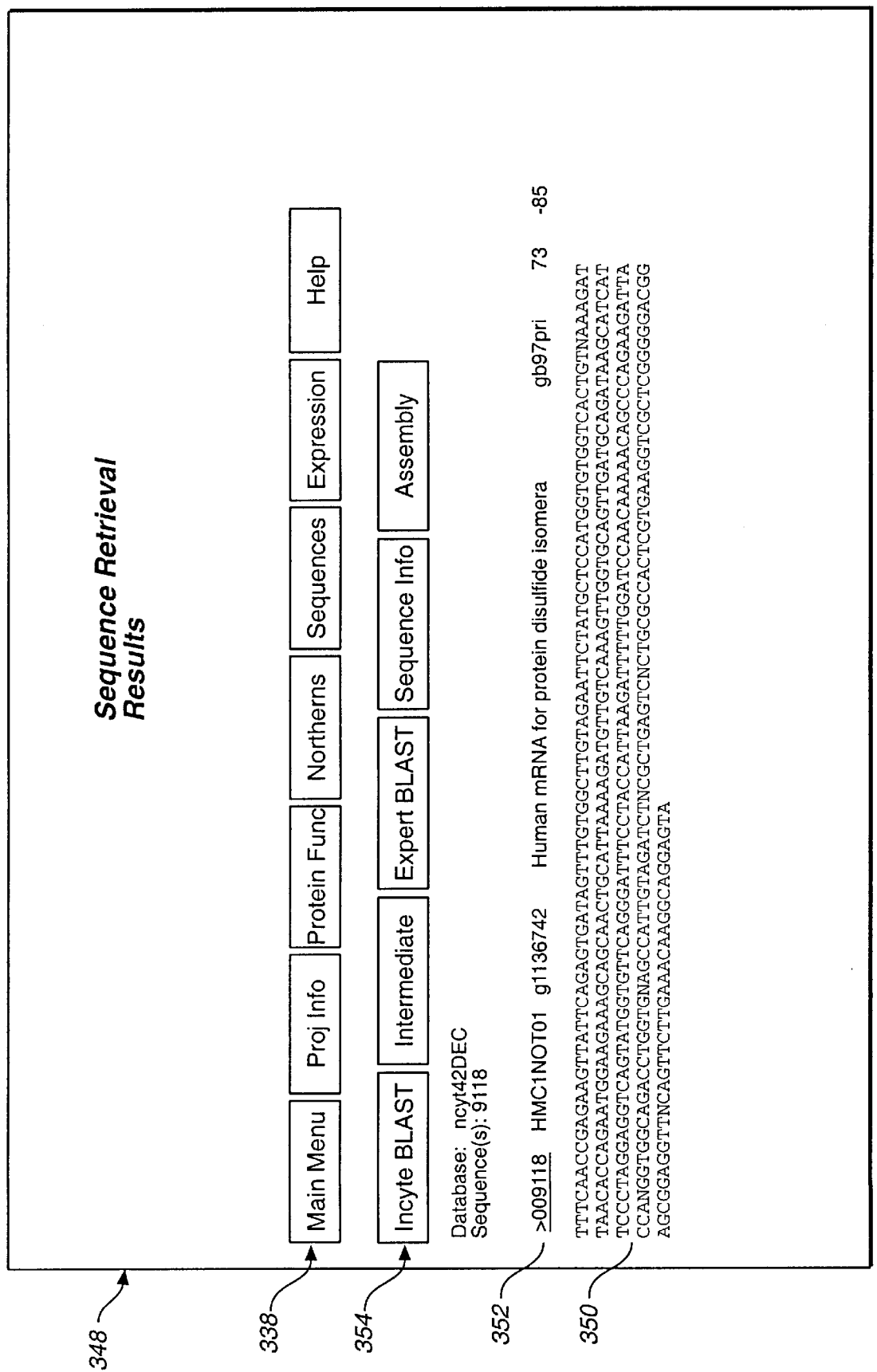
FIG._4E

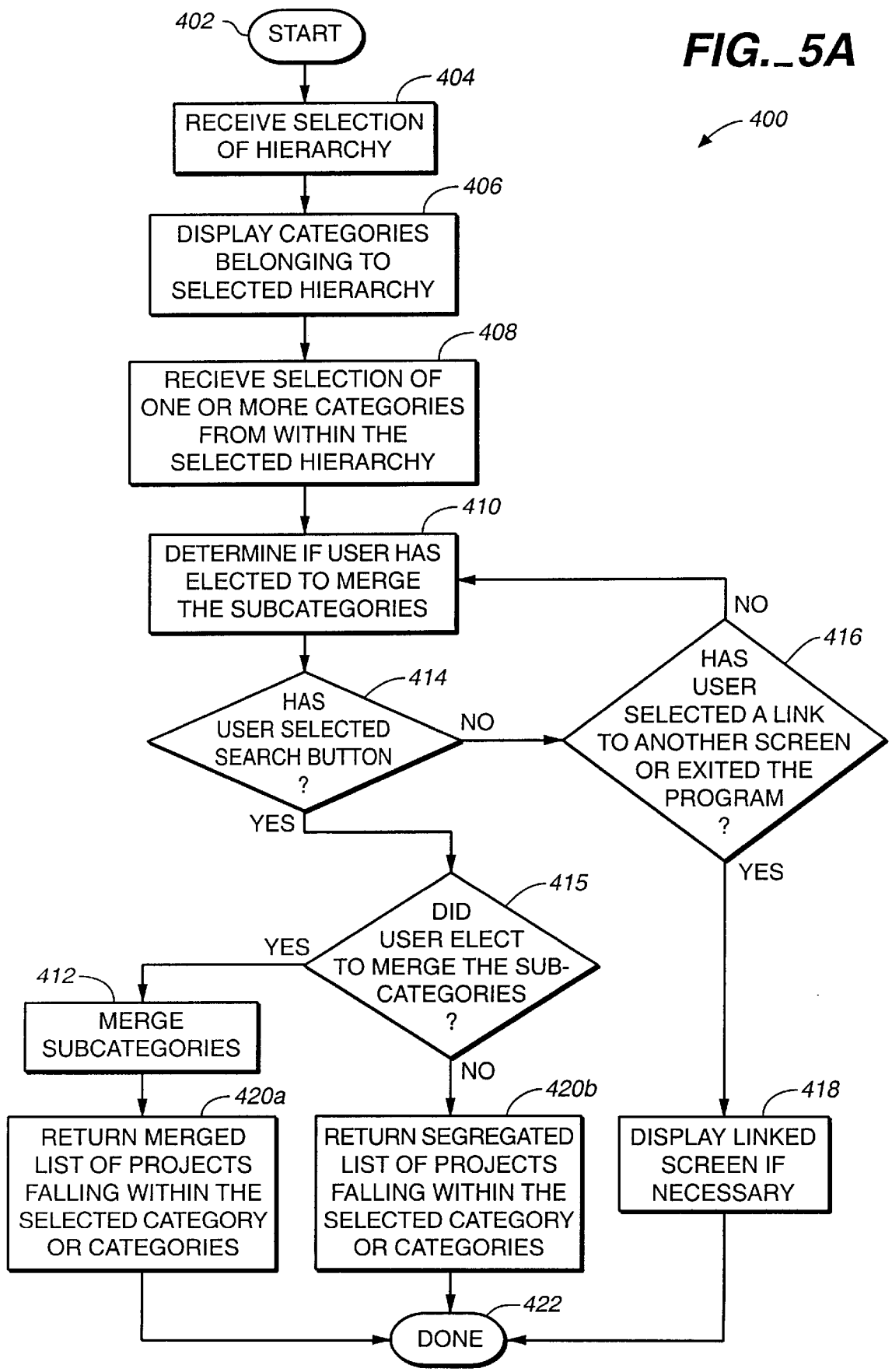
FIG._5A

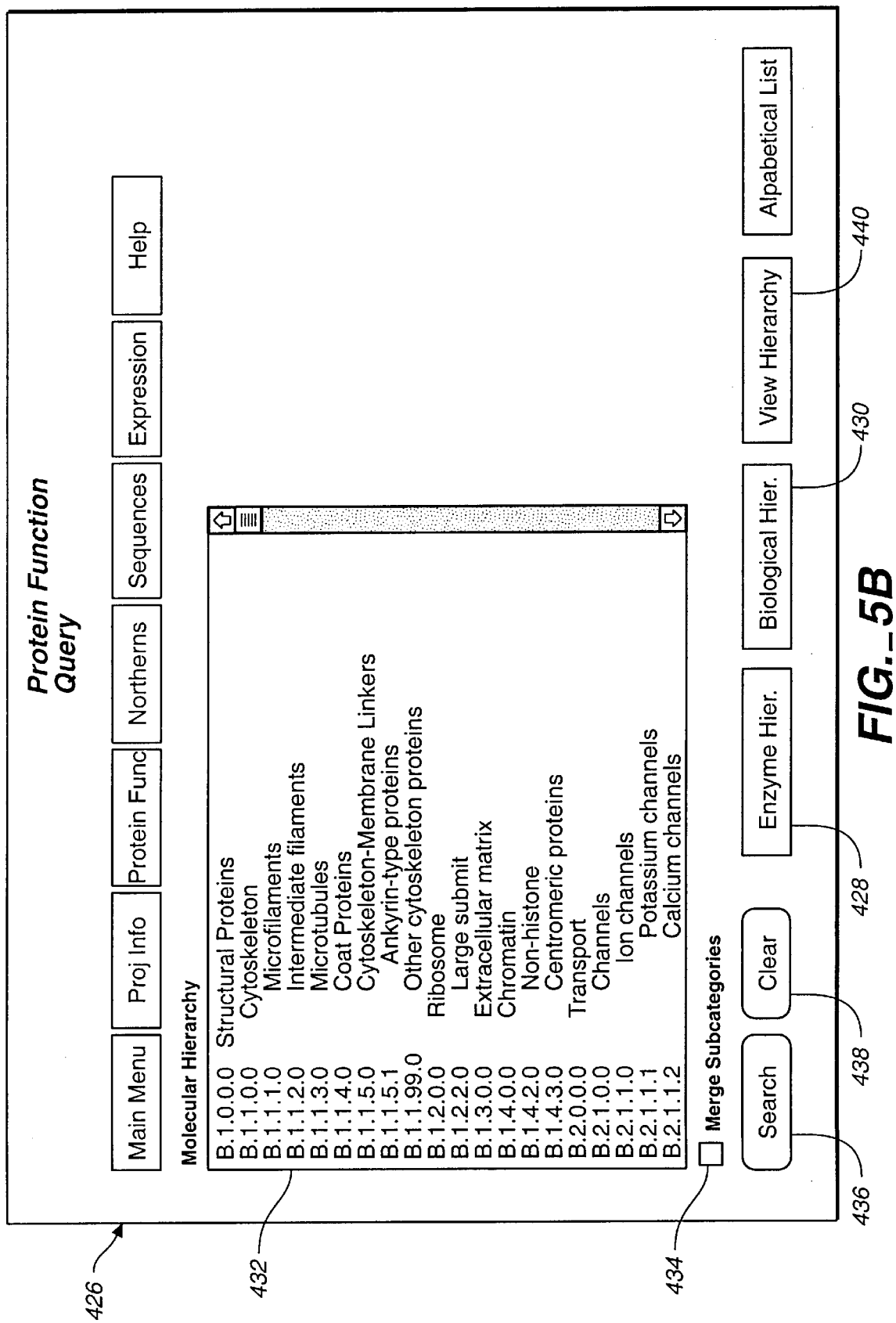
FIG._5B

Location: http://othello.incyte.com/cgi-bin/FL_ViewHierarchg?List=B

| | |
|---|---|
| B.1.0.0.0 | Structural Proteins |
| B.1.1.0.0 |   Cytoskeleton |
| B.1.1.1.0 |     Microfilaments |
| B.1.1.2.0 |     Intermediate filaments |
| B.1.1.3.0 |     Microtubules |
| B.1.1.4.0 |     Coat Proteins |
| B.1.1.5.0 |     Cytoskeleton-Membrane Linkers |
| B.1.1.5.1 |       Ankyrin-type proteins |
| B.1.1.99.0 |     Other cytoskeleton proteins |
| B.1.2.0.0 |   Ribosome |
| B.1.2.2.0 |     Large subunit |
| B.1.3.0.0 |   Extracellular matrix |
| B.1.4.0.0 |   Chromatin |
| B.1.4.2.0 |     Non-histone |
| B.1.4.3.0 |     Centromeric proteins |
| B.2.0.0.0 | Transport |
| B.2.1.0.0 |   Channels |
| B.2.1.1.0 |     Ion channels |
| B.2.1.1.1 |       Potassium channels |
| B.2.1.1.2 |       Calcium channels |
| B.2.1.1.3 |       Chloride channels |
| B.2.1.1.4 |       Sodium channels |
| B.2.1.1.99 |       Other Ion channels |
| B.2.1.99.0 |     Other channels |
| B.2.2.0.0 |   Transporters/Pumps |
| B.2.2.1.0 |     Anion transporters/pumps |
| B.2.2.2.0 |     Proton transporters/pumps |
| B.2.2.3.0 |     Calcium transporters/pumps |
| B.2.2.4.0 |     Sodium transporters/pumps |
| B.2.2.5.0 |     Potassium transporters/pumps |
| B.2.2.6.0 |     Phosphate transporters/pumps |
| B.2.2.7.0 |     Amino acid transporters/pumps |

FIG._5C

| Main Menu | Proj Info | Protein Func | Northerns | Sequences | Expression | Help |

*Project Function Results*

| ProjectID | Status | Rep SeqID | Hit ID | Hit Description | Source | BScore | PValue |
|---|---|---|---|---|---|---|---|
| B.1.4.0.0 | Chromatin | | | | | | |
| B.1.4.2.0 | Non-histone | | | | | | |
| 2013917 | first pass | 2013917H1 | g32335 | HMG2B [Homo sapiens] | genpept97 | 178 | 3.8e-18 |
| 1970544 | first pass | 1970544H1 | g666101 | high mobility group-like nuclear protein | genpept97 | 135 | 4.3e-12 |
| 617559 | first pass | 617559H1 | g171883 | high mobility group non-histone protein | genpept97 | 113 | 2.6e-10 |
| B.1.4.3.0 | Centromeric proteins | | | | | | |
| 900441 | first pass | 900441H1 | g511285 | mitotic centromere-associated kinesin |C | genpept97 | 406 | 2.7e-49 |

FL Project Function Results returned a total of 4 row(s)

*FIG._5D*

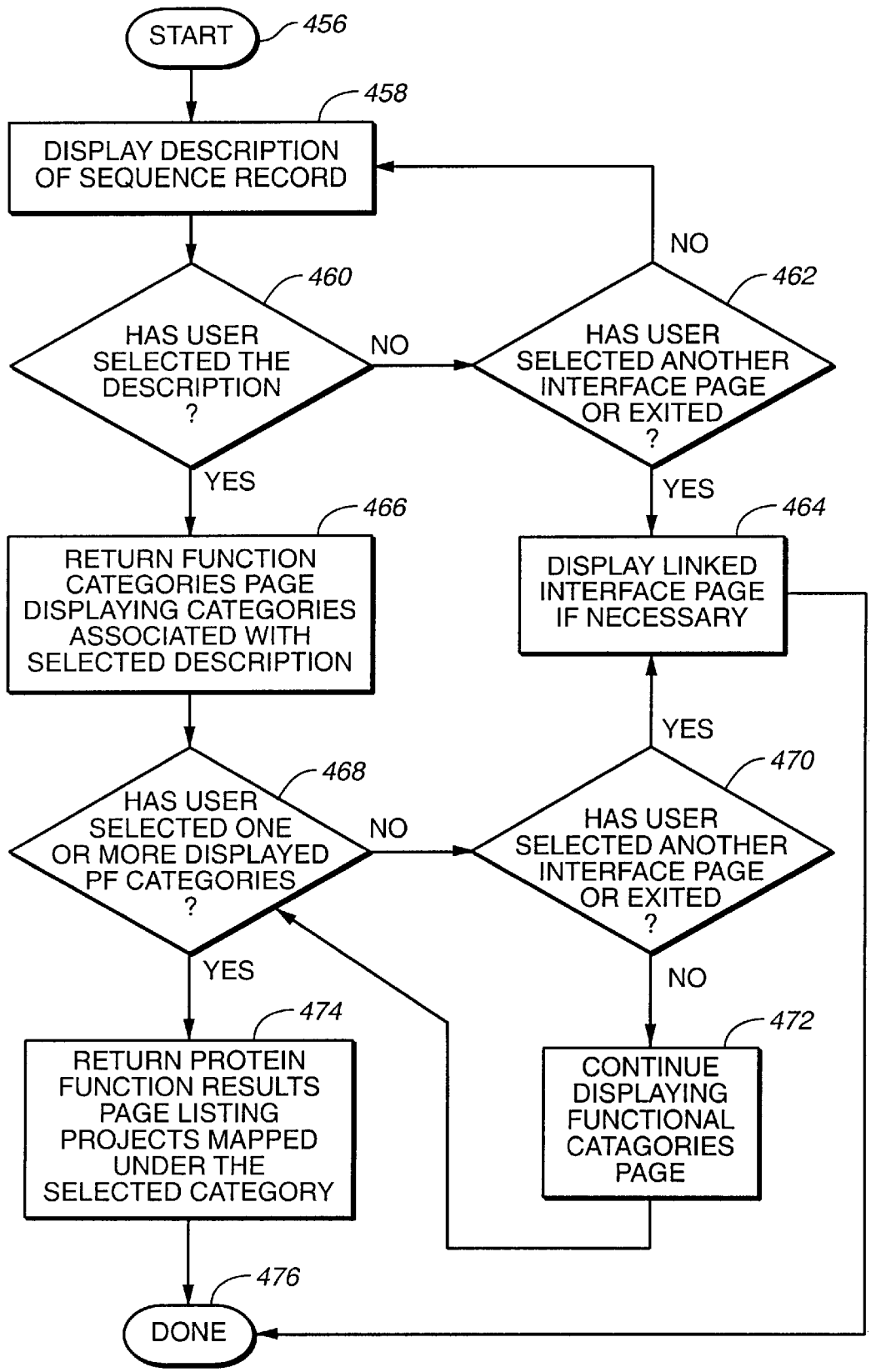
FIG._5E

*546*

Functional Catagories

| Main Menu | Proj Info | Protein Func | Northerns | Sequences | Expression | Help |

Functional Categories based on Project ID: 88307

| Category | Description |
|---|---|
| B.3.1.3.0 | Growth Factors |
| C.1.6.2.0 | Plasma membrane |
| C.2.2.0.0 | Growth and differentiation |

FL Functional Categories returned a total of 3 row(s).

FIG._5F

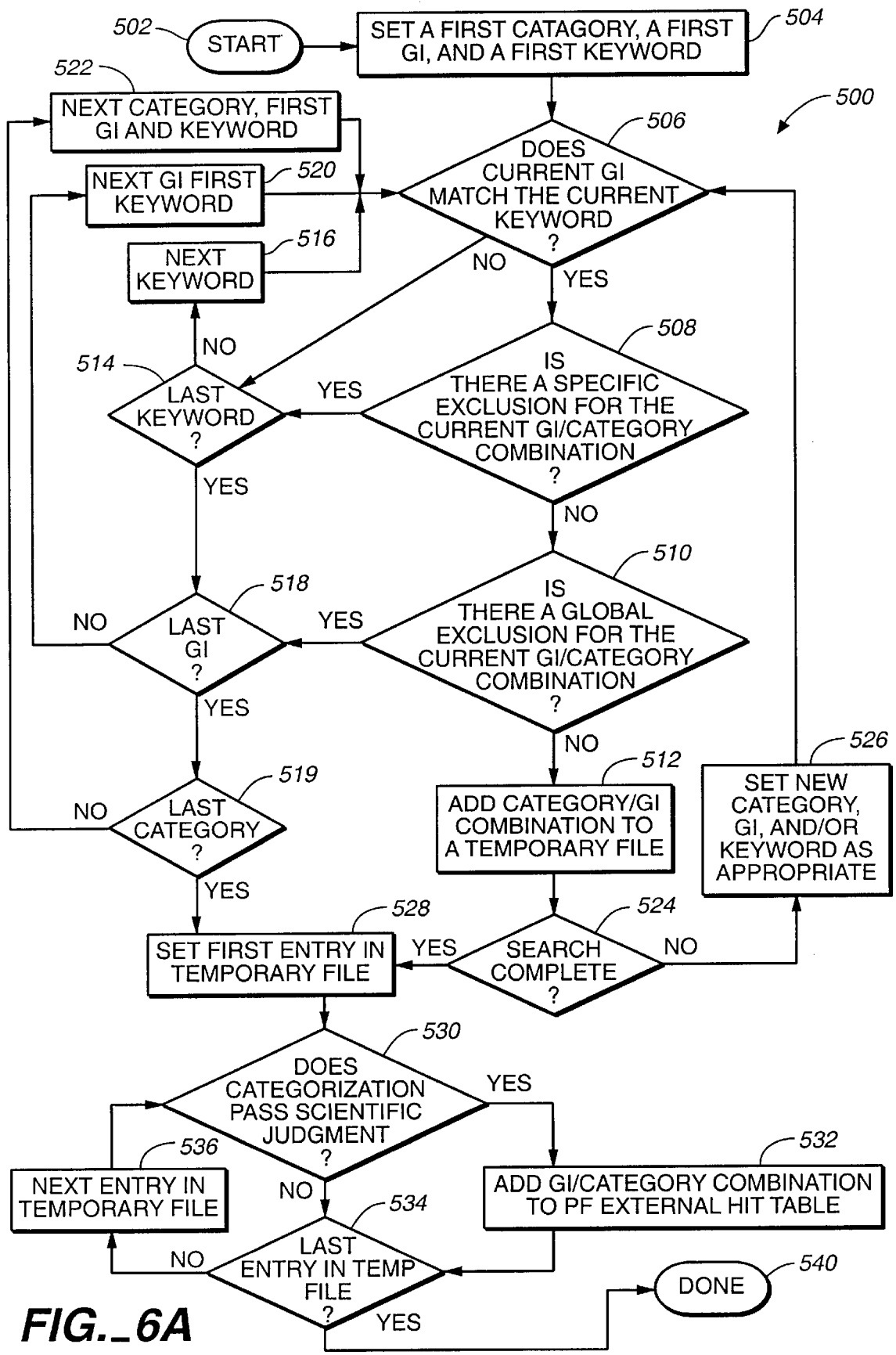
FIG._6A

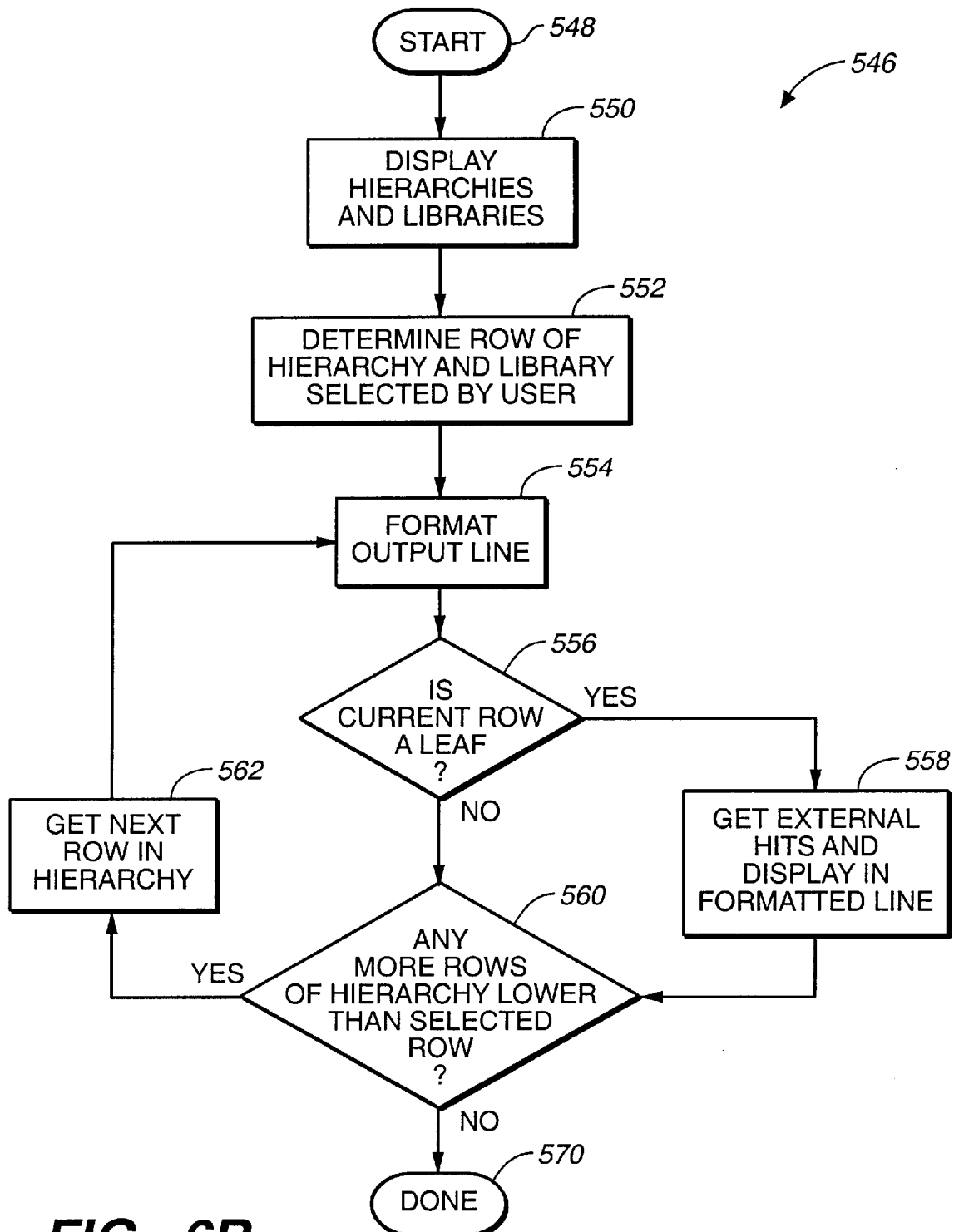
FIG._6B

DATABASE SYSTEM EMPLOYING PROTEIN FUNCTION HIERARCHIES FOR VIEWING BIOMOLECULAR SEQUENCE DATA

CROSS REFERENCE TO RELATED APPLICATIONS

This application claims priority under 35 USC § 119(e) from U.S. Provisional patent application Ser. No. 60/032,563, filed Dec. 12, 1996 and entitled DATA BASE CONTAINING FULL LENGTH NUCLEIC ACID SEQUENCES. This application also claims priority under 35 USC § 119(e) from U.S. Provisional patent application Ser. No. 60/028,284, filed Oct. 10, 1996 and entitled RELATIONAL DATABASE FOR STORING BIOMOLECULE INFORMATION. Both of these provisional applications are incorporated herein by reference in their entireties and for all purposes. In addition, this application incorporates by reference in its entirety and for all purposes application Serial No. 08/811,758 entitled PROJECT-BASED FULL-LENGTH BIOMOLECULAR SEQUENCE DATABASE, filed concurrently herewith.

BACKGROUND OF THE INVENTION

The present invention relates generally to relational databases for storing and retrieving biological information. More particularly the invention relates to systems and methods for providing full-length cDNA sequences in a relational format allowing retrieval in a client-server environment.

Informatics is the study and application of computer and statistical techniques to the management of information. In genome projects, bioinformatics includes the development of methods to search databases quickly, to analyze nucleic acid sequence information, and to predict protein sequence and structure from DNA or RNA sequence data.

Increasingly, molecular biology is shifting from the laboratory bench to the computer desktop. Today's researchers require advanced quantitative analyses, database comparisons, and computational algorithms to explore the relationships between sequence and phenotype. Thus, by all accounts, researchers cannot and will not be able to avoid using computer resources to explore gene expression, gene sequencing, and molecular structure.

One use of bioinformatics involves studying genes differentially or commonly expressed in different tissues or cell lines (e.g. normal and cancerous tissue). Such expression information is of significant interest in pharmaceutical research. The sequence tag method involves generation of a large number (e.g., thousands) of Expressed Sequence Tags ("ESTs") from cDNA libraries (each produced from a different tissue or sample). ESTs are partial transcript sequences that may cover different parts of the cDNA(s) of a gene, depending on cloning and sequencing strategy. Each EST includes about 50 to 300 nucleotides. If it is assumed that the number of tags is proportional to the abundance of transcripts in the tissue or cell type used to make the cDNA library, then any variation in the relative frequency of those tags, stored in computer databases, can be used to detect the differential abundance and potentially the expression of the corresponding genes.

To make EST information manipulation easy to perform and understand, sophisticated computer database systems have been developed. In one database system, developed by Incyte Pharmaceuticals, Inc. of Palo Alto, Calif., abundance levels of mRNA species represented in a given sample are electronically recorded and annotated with information available from public sequence databases such as GenBank. The resulting information is stored in a relational database that may be employed to establish a cDNA profile for a given tissue and to evaluate changes in gene expression caused by disease progression, pharmacological treatment, aging, etc.

While relational database systems such as those developed by Incyte Pharmaceuticals, Inc. provide great power and flexibility in analyzing gene expression information, this area of technology is still in its infancy and further improvements in relational database systems and their content will help accelerate biological research for numerous applications.

SUMMARY OF THE INVENTION

The present invention provides relational database systems for storing biomolecular sequence information in a manner that allows sequences to be catalogued and searched according to one or more protein function hierarchies. The hierarchies are provided to allow carefully tailored searches for sequences based upon a protein's biological function or molecular function. To make this capability available in large sequence databases, the invention provides a mechanism for automatically grouping new sequences into protein function hierarchies. This mechanism takes advantage of descriptive information obtained from "external hits" which are matches of stored sequences against gene sequences stored in an external database such as GenBank. The descriptive information provided with GenBank is evaluated according to a specific algorithm and used to automatically group the external hits (or the sequences associated with the hits) in the categories. Ultimately, the biomolecular sequences stored in databases of this invention are provided with both descriptive information from the external hit and category information from a relevant hierarchy or hierarchies.

The invention provides a computer system having a database containing records pertaining to a plurality of biomolecular sequences. At least some of the biomolecular sequences are grouped into a first hierarchy of protein function categories, the protein function categories specifying biological functions of proteins corresponding to the biomolecular sequences and the first hierarchy. The hierarchy includes a first set of protein function categories specifying biological functions at a cellular level, and a second set of protein function categories specifying biological functions at a level above the cellular level. The computer system of the invention also includes a user interface allowing a user to selectively view information regarding the plurality of biomolecular sequences as it relates to the first hierarchy. The computer system may also include additional protein function categories based, for example, on molecular or enzymatic function of proteins. The biomolecular sequences may include nucleic acid or amino acid sequences. Some of said biomolecular sequences may be provided as part of one or more projects for obtaining full-length gene sequences from shorter sequences, and the database records may contain information about such projects.

The invention also provides a method of using a computer system to present information pertaining to a plurality of biomolecular sequence records stored in a database. The method involves displaying a list of the records or a field for entering information identifying one or more of the records, identifying one or more of the records that a user has selected from the list or field, matching the one or more selected records with one or more protein function categories from a first hierarchy of protein function categories into which at least some of the biomolecular sequence records are grouped, and displaying the one or more categories matching the one or more selected records. The protein function categories specify biological functions of proteins corresponding to the biomolecular sequences and the first hierarchy includes a first set of protein function categories specifying biological functions at a cellular level, and a second set of protein function categories specifying biological functions at a tissue level. The method may also involve matching the records against other protein function hierarchies, such as hierarchies based on molecular and/or enzymatic function, and displaying the results. At least some of the biomolecular sequences may be provided as part of one or more projects for obtaining full-length gene sequences from shorter sequences, and the database records may contain information about those projects.

Additionally, the invention provides a method of using a computer system to present information pertaining to a plurality of biomolecular sequence records stored in a database. The method involves displaying a list of one or more protein biological function categories from a first hierarchy of protein biological function categories into which at least some of the biomolecular sequence records are grouped, identifying one or more of the protein biological function categories that a user has selected from the list, matching the one or more selected protein biological function categories with one or more biomolecular sequence records which are grouped in the selected protein biological function categories, and displaying the one or more sequence records matching the one or more selected protein biological function categories. The protein biological function categories specify biological functions of proteins corresponding to the biomolecular sequences and the first hierarchy includes a first set of protein biological function categories specifying biological functions at a cellular level, and a second set of protein biological function categories specifying biological functions at a tissue level. The method may also involve matching the records against other protein function hierarchies, such as hierarchies based on molecular and/or enzymatic function, and displaying the results. At least some of the biomolecular sequences may be provided as part of one or more projects for obtaining full-length gene sequences from shorter sequences, and the database records may contain information about those projects.

Another aspect of the invention provides a database system having a plurality of internal records. The database includes a plurality of sequence records specifying biomolecular sequences, at least some of which records reference hits to an external database, which hits specify genes having sequences that at least partially match those of the biomolecular sequences. The database also includes a plurality of external hit records specifying the hits to the external database, and at least some of the records reference protein function hierarchy categories which specify at least one of biological functions of proteins or molecular functions of proteins. At least some of the biomolecular sequences may be provided as part of one or more projects for obtaining full-length gene sequences from shorter sequences, and the database records may contain information about those projects.

Further aspects of the present invention provide a method of using a computer system and a computer readable medium having program instructions to automatically categorize biomolecular sequence records into protein function categories in an internal database. The method and program involve receiving descriptive information about a biomolecular sequence in the internal database from a record in an external database pertaining to a gene having a sequence that at least partially matches that of the biomolecular sequence. Next, a determination is made whether the descriptive information contains one or more terms matching one or more keywords associated with a first protein function category, the keywords being terms consistent with a classification in the first protein function category. When at least one keyword is found to match a term in the descriptive information, a determination is made whether the descriptive information contains a term matching one or more anti-keywords associated with the first protein function category, the anti-keywords being terms inconsistent with a classification in the first protein function category. Then, the biomolecular sequence is grouped in the first protein function category when the descriptive information contains a term matching a keyword but contains no term matching an anti-keyword.

These and other features and advantages of the invention will be described in more detail below with reference to the drawings.

BRIEF DESCRIPTION OF THE DRAWINGS

FIG. 1A is an illustration of a library having multiple clones, one of which will be selected as a "birth clone."

FIG. 1B is an illustration of various sequences relevant to a project including a gene, a first pass sequence, the birth clone, forward and reverse long read sequence, assemblages, and a full-length sequence.

FIG. 1C is an illustration of how various projects are merged, if during the course of sequencing work it becomes apparent that two or more projects relate to the same gene.

FIG. 1D is an illustration of various sequence matches and associated "product scores" representing the strengths of the sequence matches.

FIG. 2A is a block diagram of a client-server Intranet for providing database services in accordance with one embodiment of the present invention.

FIG. 2B is a schematic representation of the various software documents entities employed by the FIG. 2A client-server Intranet to provide biological information in response to some user queries.

FIG. 3 is a physical data model for a gene expression relational database containing full-length cDNA sequences in accordance with a preferred embodiment of the present invention.

FIG. 4A is a screen (HTML page) display presenting a Main Menu for a graphical user interface of a full-length sequences database in accordance with one embodiment of the present invention.

FIG. 4B is a Project Information Query screen allowing users to enter queries about particular projects or sequences within projects.

FIG. 4C is a Project Information Results screen for displaying project information generated by the full-length sequences database in response to user queries formulated on the screen of FIG. 4B.

FIG. 4D is a Sequence Information Results screen presenting sequences associated with a particular project.

FIG. 4E is a Sequence Retrieval Results screen for displaying actual amino acid or nucleotide sequences of a selected project sequence.

FIG. 5A is a process flow diagram of a user interface process by which a user can identify all projects in a database that have sequences matching a selected protein function category.

FIG. 5B is a screen shot of a user interface HTML page provided for accepting user queries pertaining protein functions.

FIG. 5C is a screen shot of a user interface HTML page provided to display of a view of a selected protein function hierarchy.

FIG. 5D is a screen shot of a user interface HTML page provided to display the results of a user's protein function query.

FIG. 5E is a process flow diagram of a process by which a user can identify the protein function categories associated with a selected sequence.

FIG. 5F is a screen shot of a user interface HTML page provided to display all the protein functional categories associated with a selected project.

FIG. 6A is a process flow diagram presenting the steps employed to classify sequences in a protein structure hierarchy.

FIG. 6B is a process flow diagram presenting the steps employed to process user queries directed at the protein structure hierarchy.

DETAILED DESCRIPTION OF THE PREFERRED EMBODIMENTS

1. Introduction and Relevant Terminology

Generally, the present invention provides an improved relational database for storing sequence information. The invention may be employed to investigate data from various sources. For example, it may catalogue animal sequences (e.g., human, primate, rodent, amphibian, insect, etc.), plant sequences, and microbial sequences. In the following description, numerous specific details are set forth in order to provide a thorough understanding of the present invention. It will be apparent, however, that the present invention may be practiced without limitation to some of the specific details presented herein.

The following terms are used throughout the specification. The descriptions are provided to assist in understanding the specification, but do not necessarily limit the scope of the invention.

Internal database—This is the focus database of this invention. It contains biomolecular sequences associated with a project. It may also contain information associated with sequences such as the library in which a given sequence was found, descriptive information about a likely gene associated with the sequence, etc. The database may divided into two parts: one for storing the sequences themselves and the other for storing the associated information. This database may sometimes be referred to a "local" or "enterprise" database.

The internal database may typically be maintained as a private database behind a firewall within an enterprise. However, this invention is not so limited and the internal database could actually be made available to the public. The internal database may include sequence data generated by the same enterprise that maintains the database, and may also include sequence data obtained from external sources. Examples of private internal databases include the LifeSeq™ and LifeSeq FL™ databases available from Incyte Pharmaceuticals, Inc. of Palo Alto, Calif.

Sequence database—When the internal database is designed to include separate parts, one of these may be a sequence database which contains sequences of biomolecules in the internal database.

Gene expression database—When the internal database is designed to include separate parts, one of these may be a gene expression database containing annotation information about sequences in sequence database. As noted, such information may include the library in which a given sequence was found, descriptive information about a related cDNA(s) associated with the sequence, etc.

External database—This is a database located outside the internal database. Typically, it will be maintained by an enterprise that is different from the enterprise maintaining the internal database. In the context of this invention, the external database is used primarily to obtain information about the various sequences stored in the internal database. The external database may be used, for example, to provide some descriptive information stored in the gene expression database. In a preferred embodiment, the external database is GenBank and associated databases maintained by the National Center for Biotechnology Information (NCBI), part of the National Library of Medicine. GenPept is the associated public protein-sequence database that contains all the protein databases from GenBank. Other examples of external databases include the Blocks database maintained by the Fred Hutchinson Cancer Research Center in Seattle and the Swiss-Prot site maintained by the University of Geneva.

Record—This term generally refers to a row in a database table. Each record contains one or more fields or attributes. A given record may be uniquely specified by one or a combination of fields or attributes known as the record's primary key.

Gene—As generally used herein, refers to a cDNA transcript of a mRNA which codes for a complete protein. The mRNA is a transcript of the coding portions of a genomic DNA gene sequence.

Library—A collection of expressed genes, with annotations, from a specific tissue or other sample.

Full-length project or just "project"—This describes one or more sequences associated with an enterprise effort to identify the entire sequence of a gene. A project is created when a clone is identified as encoding at least of a portion of a potentially interesting protein. Such a clone, referred to as the birth clone, enters a full-length sequencing program having as its goal elucidation of the full sequence of the gene containing the birth clone. As the project evolves, multiple sequences become part of the project. The birth clone becomes the first member of a project. Eventually, 5' complete sequences, assemblages of sequences, and ultimately a full-length sequence may become members of the project. Each project has a representative sequence which is generally the best consensus sequence (e.g., a full-length sequence). To simplify cataloging the projects, each project includes a unique ProjectID which is an ID number related to the project's birth clone.

First pass sequence—This is a project member having the project's initial sequence (e.g., a sequenced cDNA fragment of a gene of interest). In one embodiment it is obtained from high-throughput sequencing (HTPS). It may be an EST that has been identified as being derived from or homologous to a potentially interesting gene. It describes a partial sequence of the birth clone. In one embodiment the first pass sequence corresponds to a nucleotide alignment in GenBank but does not contain the start of a coding sequence; or has a protein alignment but does not contain the amino-terminal end of a GenPept sequence.

Assemblage—This is a project member providing a sequence (e.g., cDNA) that contains more information than the initial project sequence but is not yet full-length. The added sequence may come from assembly of overlapping clones (including the birth clone). Alternatively, additional sequences may be obtained from extension cloning or from long-read sequencing.

Long read sequence—This is a sequence of the birth clone generated from either the 3' (using e.g., M13-21 primer) or 5' (using e.g., M13 reverse primer) ends of the mRNA. If the birth clone is short enough, the forward and reverse long read sequences may overlap, thereby providing a complete sequence of the birth clone. The forward and reverse long read sequences may also be assembled with the first pass sequence to help elucidate the full birth clone sequence.

5' complete sequence—This is a project member having a sequence (e.g., cDNA) that presumptively contains the 5' terminus of the gene. In one embodiment, the 5' complete sequence is recognized as having a nucleotide alignment containing an annotated start of a coding sequence feature in GenBank or a protein alignment containing the amino-terminal end of a GenPept sequence (novel homologue or exact match).

Full-length sequence—This is a project member having an entire gene sequence coding for a polypeptide sequence. The full sequence may be recognized as one having an alignment matching the N- and C-termini of a public sequence (for example from GenPept). The match need not be exact, and may simply specify a novel homologue. The full-length sequence may be recorded as a cDNA sequence or, alternatively, as the full mRNA sequence or amino acid sequence of a polypeptide encoded by the full mRNA sequence.

Cluster—This is a group of clones related to one another by sequence homology. In one example, clusters are formed based upon a specified degree of homology and overlap (e.g., a stringency (Product Score described below) of >=50 and <=100). A project's full-length sequence may be compared against sequences from other clones (e.g., first-pass sequences in the internal database). When a sequence from the internal database overlaps part of a full-length sequence, the internal database sequence becomes part of the same project as its related full-length sequence. This allows researchers to identify clusters of related gene sequences.

Biological function—this describes the global or biological behavior and effects of a protein or peptide. Generally, a protein's biological function does not directly specify its structure or functioning at a molecular level. Rather, it specifies the protein's behavior at at least the cellular level. Examples include "cell cycle" and "DNA repair." In addition, the biological function may specify a protein's function in an even more global context such as the tissue level or the organism level. An example of a tissue level category is "apoptosis," and an example of an organism level category is "development."

Molecular function—this describes the local or chemical behavior of a protein or peptide. Generally, a protein's molecular function does not account for its functioning at biological level (e.g., a cellular, tissue, or organismal level). In fact, the molecular function may often be the same in vitro and in vivo. Examples of molecular function include "microfilaments," "chromatin" and "calcium channels."

2. Data Flow for Populating the Gene Expression Relational Database

The following description presents one preferred method for generating and collecting sequence data for a project. FIGS. 1A and 1B help illustrate the process.

Selection and processing of sequences for a database of the present invention begins by identifying a promising candidate sequence which may constitute less than a full gene sequence. Criteria for selecting such candidate sequence will be further described below. In one approach, a candidate sequence for a new project is obtained by analysis of sequence data found in an existing sequence database, for example, the LifeSeq™ database developed by Incyte Pharmaceuticals, Inc., of Palo Alto, Calif. Generally, such a source database will be populated by specifically identified and catalogued cDNA clones. An example of one process by which data for a source database may be obtained is as follows.

Messenger RNA (mRNA) is extracted from a sample under consideration (e.g., a particular tissue or cell line) and fully-complex cDNA libraries are constructed. Preferably, these libraries are generated by molecular cloning techniques well known in the art. These techniques make use of the principal flow of expressed genetic information from genomic DNA, to mRNA, to protein. That portion of a genomic DNA sequence which is ultimately expressed as protein is first converted (transcribed) to corresponding (and complementary) mRNA sequences. These mRNA sequences, representing a cell's genes, are extracted from other cellular materials by known techniques, such as affinity chromatography.

A typical cell may contain 10,000 to 30,000 unique mRNA transcripts. For complex tissues (such as brain), this number can be 100,000 or greater. Further, there are three abundance (or prevalence) classes of mRNA; (1) high (super-prevalent) species which exist at greater than 10,000 copies per cell; (2) middle (prevalent) species which exist at 100 to 400 per copies per cell; and (3) low (rare) species which are found at less than 15 unique transcripts per cell.

Clone libraries are composed of complementary DNA (cDNA). Techniques for synthesis of first-strand cDNA from mRNA are well known in the art. One suitable technique is initiated by using (1) a poly-deoxythymidine (poly-dT) primer oligonucleotide that is complementary to the characteristic poly-adenosine (poly-A) tail at the 3' end of most eukaryotic mRNA transcripts; and (2) the reverse transcriptase enzyme. Preferably, the primer used in this reaction also contains a restriction enzyme recognition cite (e.g., Not1) that permits insertion of the appropriate cloning vector. Second-strand cDNA synthesis may employ RNase to nick the mRNA/cDNA hybrid created in the reverse transcription reaction, creating priming cites for *E. coli* DNA polymerase to create second-strand cDNA. The gaps in the second strand may then be ligated together using *E. coli* DNA ligase.

After the ends of the cDNA are blunted with, for example, T4 or Pfu DNA polymerase, an adapter may be ligated into the double-stranded cDNA. This oligonucleotide, which contains a second enzyme restriction cite (usually EcoR1 or Sal1), allows for directional cloning of the cDNA once digestion is complete with the initial enzyme restriction cite (e.g., Not1) found at the 3' terminus of the cDNA. The cDNA is then size-fractionated to remove very short cDNAs which would inhibit the ability to generate highly complex libraries. Thereafter, the cDNAs, which, for the most part are complementary sequences of portions of mRNAs which code for proteins, are ligated into a plasmid vector Sequencing is an adaptation of the natural process of DNA replication. Therefore, it requires template and primer sequences. One general template preparation and sequencing protocol begins with automated picking of bacterial colonies, each of which contains a separate cDNA clone which will function as a template for the sequencing reaction. The selected colonies are placed into media, and grown overnight. The cDNA templates are then purified from the cells and suspended in water. After DNA quantification, high-throughput sequencing is performed using a sequencers, such as Applied Biosystems, Inc., Prism 377 DNA Sequencers. These "first pass," or "high-throughput"

sequences are generally a partial sequence of their associated clone, starting from the 5' end of the clone. They are unique identifiers of their respective clones, and are sometimes referred to as expressed sequence tags (ESTs). As mentioned, an EST is generally about 50–300 nucleotides in length and, depending on cloning and sequencing strategy, may cover all, but more frequently a fraction, of the gene sequence. The cDNA clones from which ESTs are derived are generally part of libraries, each of which represents a collection of genomic information expressed for a given tissue or sample. Typically, libraries containing more than 1 million clones are generated. FIG. 1A is a representation of a cDNA clonal library 1, showing the cDNA clonal inserts 2 expanded from the vector portions 4 of the clones.

In order to analyze and manipulate EST information, sophisticated computer relational database systems have been developed, for example, the aforementioned LifeSeq™ database developed by Incyte Pharmaceuticals, Inc., of Palo Alto, Calif., which was described in U.S. Provisional patent application Ser. No. 60/028,284, filed Oct. 10, 1996, the disclosure of which was previously incorporated by reference.

The database of the present invention is concerned with full-length gene sequences and the information generated during discovery of such full-length gene sequences. ESTs representing clones of genes of interest are selected from a source database (e.g., part of an internal database) based on several criteria. Genes of interest may include those which relate to interesting patterns of expression, such as those associated with particular biochemical functions or disease states. ESTs which demonstrate some homology to existing genes of interest, but for which no data exists in public databases are frequently selected. Moreover, genes in the rare and sometimes the prevalent abundance categories are generally selected since those genes are more likely to be tissue or system specific.

Various elements of the process for generating full-length sequences for the database of the present invention are illustrated in FIG. 1B. As noted, each full-length gene sequencing effort undertaken in conjunction with the database of the present invention is termed a "project." Each project begins with a cDNA clone 10 (represented in FIG. 1B by its sense strand) corresponding to an EST 15 selected from the source database. The EST sequence in a project may be denoted "H1" as shown in FIG. 1B. "H" stands for high throughput sequencing and "1" stands for the first such sequence in the project.

Clone 10 is generally a partial cDNA transcript of an mRNA 20 which codes for a complete protein. , and may be termed a "birth clone." For convenience, this birth clone 10 may retain the sequence ID number assigned to it in the source database or library from which it is taken. Each project may be initially identified by its birth clone ID.

A full-length sequencing project begins with a determination of whether or not the 5' end of the EST 15 incorporates or is close to the 5' end of the mRNA 20. If this is the case, it indicates that the birth clone likely contains the entire coding region of the gene of interest, and it is a simple matter to sequence the entire length of the clone by the long-read, and possibly the sub-cloning methods described below. More frequently, however, the 5' end of the EST will not correspond to the 5' end of the mRNA, and further steps will be required to determine the complete sequence of the gene.

In either event, the first step in the full-length sequencing process is long-read sequencing from both the 5' and 3' ends of the birth clone. Long-read sequencing uses primers (e.g., M13-21 primer gives 3' ("reverse") sequence and M13 reverse primer gives 5' ("forward") sequence) complementary to the known vector sequences adjacent to the cDNA clonal insert, and generally has an approximately 600 base read length due to sequence reaction conditions and electrophoretic gel resolution limitations. When a birth clone is approximately one kilobase (kb; 1000 bases) in length, long-read sequencing from both ends of the clone will generally be sufficient to determine the entire sequence for the clone, since the ends of a 5' long-read sequence 30 and a 3' long-read sequence 35 obtained will overlap in the middle of the birth clone sequence. The project's first forward long read sequence in a project is denoted "F1" and its first reverse long read sequence is denoted "R1."

When the 5' long-read sequence 30 and the 3' long-read sequence 35 do not overlap, it is an indication that the birth clone may be more than approximately 1 kb in length. In this case, the sequence of the birth clone may be determined by well known molecular biological techniques such as subcloning, which breaks the birth clone into smaller pieces, followed by long-read sequencing to determine the complete sequence of each sub-clone (not shown). The sequences of these sub-clones may then be combined to obtain a complete consensus sequence of the original birth clone. Alternatively, full length sequence coverage may be obtained from other cDNA library sequences, such as those found in the previously noted LifeSeq™ database developed by Incyte Pharmaceuticals, Inc., of Palo Alto, Calif. The consensus sequence of the birth clone obtained by subcloning and/or forward and reverse long reads may be denoted "C."

Generally, the birth clone will include coverage of the 3' end of the cDNA. This may be confirmed by the presence of several consecutive thymidine nucleotides 12 at the 3' end of the antisense strand of the clone (not shown). These nucleotides are complementary to the characteristic poly-A nucleotide tail 22 present on the 3' end of mRNA transcripts. The 3' end of the clone is present in virtually all birth clones since the presence of the distinctive poly-A tail 22 in mRNA is used to design a complementary poly-T oligonucleotide primer as an initiation point for cDNA synthesis. However, some cDNAs will generally be generated using a random primer, and will therefore not have a poly-A tail.

Once the presence of the birth clone's 3' end is confirmed, the sequencing project continues towards the 5' end of the cDNA clone. "Extension" of the birth clone 10 into the full expression sequence of the gene may be conducted in a number of ways. In one method, two primers 40 are designed to correspond to the ends of the of the known birth clone sequence and to anneal to DNA in a cDNA library so as to initiate extension away from the known cDNA sequence. The primers are added to a cDNA library with appropriate enzymes and extend through additional DNA sequence to produce PCR products 42, 44, 46. These PCR products are subsequently purified and sequenced to provide new sequences 50, 52, 54. The new sequences are then compared with the known partial cDNA sequence for areas of overlap, and the sequence is extended beyond the overlapping areas to provide longer DNA sequence. This technique is described more fully in U.S. patent application Ser. No. 08/487,112, filed Jun. 7, 1995, entitled "Method for Obtaining Full-Length cDNA Sequences," which is incorporated by reference herein in its entirety.

In addition, it may be possible to extend the birth clone 10 by comparing its now known sequence against internal or external sequence databases (for instance, using a BLAST searching algorithm) in order to locate homologous sequences (e.g., sequences 60 and 62 in FIG. 1B) which cluster with or overlap with the known birth clone sequence.

The extension sequences may be identified as containing the 5' terminus of the full mRNA sequence by comparing extension sequences' 5' ends with those of the known gene associated with the project. For example, if the first pass EST was selected for the project based upon its match to GenBank gene, then the 5' ends of the extension sequences are compared against the corresponding end of the most closely related GenBank gene (or an amino terminus of a corresponding protein). If there is a strong homology, then it is assumed that the 5' end of the project's gene has been located.

Sequences in addition to the birth clone determined either by molecular cloning and sequencing methods or by additional database searching are assembled with the original birth clone to construct a consensus sequence 70 that is the full sequence of the gene. Except where the birth clone contains the entire sequence of a cDNA, the consensus sequence 70 will be an electronic sequence, existing as a composite sequence of discrete cDNA fragments generated from more than one template. Based on this sequence, however, an actual clone of the gene sequence may be synthesized by known methods. This physical gene clone may then be used in the laboratory for expression of the protein and functional assays for product (i.e., drug) development.

In a particular embodiment of the present invention, cDNA sequences which contain more information than the birth clone, but which are not yet full-length may be specifically identified. These sequences may be assemblages of clustering or overlapping of additional clones from internal or external databases or from extension cloning and further long-read sequencing. As noted above, in this particular embodiment, a cDNA sequence which is less then a full-length sequence, but which contains a nucleotide alignment corresponding to an annotated start of a coding sequence having a protein alignment containing the amino-terminal end of a GenPept sequence, is referred to as 5' complete. A sequence is considered full-length once it has been assembled and edited and it has been confirmed that the sequence codes for a polypeptide sequence with an alignment matching the N-terminus and C-terminus of a GenPept sequence (novel homologue or exact match).

There are generally several separate concurrent projects proceeding in conjunction with the database of the present invention attempting to sequence genes from birth clones. Sometimes, as these projects progress, it becomes clear that two birth clones are in fact part of the same gene. In this event, the two projects will be merged and will continue under the ID of the project that has been most active, for example. This process is illustrated in FIG. 1C where ProjectIDs 37521 and 57280 are merged into ProjectID 8118 as time proceeds from the bottom to the top of the figure.

Throughout these projects, sequence data may be continuously provided to the database of the present invention where a user of the database may retrieve, analyze and manipulate information about a particular birth clone, extension or project even before the full-length sequence of the gene has been determined. The new sequences may be continuously compared (e.g., using a BLAST algorithm) against external (e.g., public, such as GenBank) databases and annotated based on located matches ("hits"). Sequences for which no matches are located may be identified, usually as a unique sequence, with a proprietary designation.

"Clustering" may be performed with the sequence data after or prior to the determination of the full-length sequence of the gene. For instance, a sequence thought to be associated with a particular molecular or biological function in one tissue might be compared (e.g., using a BLAST algorithm) against another library or database of sequences. This type of search, an electronic version of the analogous molecular biological technique known as Northern blotting, is useful to look for homologous, and presumably functionally related, sequences in other tissues or samples. The sequences showing sufficient homology with the representative project sequence are considered part of a "cluster" and become associated with the project.

A number of computer platforms can be used to perform the necessary calculations for various algorithmic processes employed in the project (e.g., assembling and clustering the sequences). For example, a number of computer workstations from a variety of manufacturers can be used. In particular, workstations produced by Silicon Graphics, Inc. (SGI) of Mountain View, Calif. and multiprocessor (e.g. 12 processor) Alpha™ systems manufactured by Digital Electronics Corporation (DEC) of Maynard, Mass. have been found to be suitable for performing such calculations.

3. Matching Techniques

As noted above, the assembling and clustering (whether or not used for assembling) techniques employed in a project require some mechanism for assessing the homology and overlap of two sequences. Various techniques may be employed for this purpose and some will now be described. These techniques may also be employed to assess the strength of a match or "hit" of an internal database sequence in an external database.

Generally, for clustering/matching to be valid, two sequences should possess overlap regions of identical base pairs or at least close homology. To discover such overlap, the clustering/matching procedure may employ a sequence alignment algorithm such as BLAST (Basic Local Alignment Search Tool) or the Smith-Waterman algorithm. Both of these algorithms look for regions of ungapped similarity between two sequences (although Smith-Waterman handles gaps rather well). To do this, they determine (1) alignment between similar regions of the two sequences, and (2) a percent identity between sequences. The alignment is calculated by matching, base-by-base, the regions of substantial similarity. In these regions, identical bases are scored with a value of +5 and mismatched bases are scored with a value of −4 (for nucleic acids). Regions of contiguous bases having sufficiently high score are deemed High Scoring Pairs ("HSPs"). In BLAST, the score of the best HSP (referred to as the BLAST Score) is presented as an output. In addition, for each HSP, the percent identity is calculated and presented as a BLAST output, as is the alignment. Finally, a P-Value for each HSP is calculated. As is known to those of skill in the art, the P-Value represents the probability that the observed similarity resulted from a random occurrence. Lower P-Values indicate a greater confidence that the observed similarity is not due to a random event.

In a preferred embodiment, each new sequence is compared to every usable sequence already in the internal database using BLAST. An ad hoc score, called the "Product Score," is calculated for every matched pair of sequences. The Product Score represents a normalized summary of the BLAST output parameters and is used to represent the quality of an alignment between a query and matched sequence.

Specifically, the Product Score is a normalized value between 0 and 100 indicating the strength of a BLAST match; it represents a balance between fractional overlap and quality in a BLAST alignment. For nucleic acids, the Product Score is calculated by dividing the BLAST score by 5 times the length of the shorter of the two sequences being compared, then multiplying this result by the Percent Identify over the BLAST alignment. The expression for product score is PS=(BLAST Score·Percent Identity)/(5·minimum(length(Seq1),length(Seq2)))

As shown, the BLAST score is divided by 5 and then multiplied by the Percent Identity over the BLAST alignment. Dividing this number by the length of the shorter sequence (including all HSPs) normalizes the score such that a perfect alignment (over the entire length of the shorter sequence) gives a Product Score of 100.

For a protein match, the Product Score is adjusted by multiplying the minimum length value by 3 (the equivalent of the corresponding codon triplet) and using the typical BLAST match score for proteins (approximately 5.3).

Because the Product Score is derived from BLAST alignments, it is sensitive to (1) fraction overlap, (2) percent identity, and (3) insertions and deletions. It attempts to balance fraction overlap with the Percent Identity in an alignment. The greater the overlap in the alignment, the lower the Percent Identity needed to reach a given Product Score. Referring to FIG. 1D, a Product Score of 100 is produced only for 100% identity over the entire length of the shorter of the two sequences being compared. A Product Score of 70 can be produced either by 100% identity and 70% overlap at one end, or by 88% identity and 100% overlap at the other. Similarly, a Product Score of 50 is produced by the range of alignments between 100% identity and 50% overlap, and 79% identity and 100% overlap. A Product Score of 30 would be produced by alignments between 100% identity and 30% overlap, and 69% identity and 100% overlap.

In a preferred embodiment, the Product Score serves two purposes. First, it is used in the clustering process to measure the quality of a match between all possible pairs of sequences. Sequences that overlap with a Product Score greater than a particular "stringency threshold" (50 or 70 in a specific embodiment) are grouped as members of the same cluster. Second, it represents the quality of the match between a sequence and its naming GI (i.e., GenBank sequence identifier). Preferably, the Product Scores associated with this second calculation are stored in the gene expression database.

In sequence clustering, if a BLAST match has a Product Score above the given specified stringency, then the two matched sequences will be in the same cluster. If two sequences are not in the same cluster, then they do not match with a Product Score above the stringency threshold. The higher the Product Score threshold, the more stringent the criteria for clustering. Thus, at stringency 70, fewer sequences will cluster (and the total number of clusters will be greater) than at stringency 50.

Other clustering measures besides product score may be employed. Examples of such techniques are described in United States Provisional patent application Ser. No. 60/028,284, previously incorporated by reference.

4. The Database Environment

FIG. 2A depicts a network system 130 suitable for storing and retrieving information in relational databases of the present invention. Network 130 includes a network cable 134 to which a network server 136 and clients 138a and 138b (representative of possibly many more clients) are connected. Cable 134 is also connected to a firewall/gateway 140 which is in turn connected to the Internet 142.

Network 130 may be any one of a number of conventional network systems, including a local area network (LAN) or a wide area network (WAN), as is known in the art (e.g., using Ethernet, IBM Token Ring, or the like). The network includes functionality for packaging client calls in a well-known format (e.g., URL) together with any parameter information into a format (of one or more packets) suitable for transmission across a cable or wire 134, for delivery to database server 136.

Server 136 includes the hardware necessary for running software to (1) access database data for processing user requests, and (2) provide an interface for serving information to client machines 138a and 138b. In a preferred embodiment, depicted in FIG. 2A, the software running on the server machine supports the World Wide Web protocol for providing page data between a server and client.

Client/server environments, database servers, and networks are well documented in the technical, trade, and patent literature. For a discussion of database servers and client/server environments generally, and SQL servers particularly, see, e.g., Nath, a., *The Guide To SQL Server*, 2nd ed., Addison-Wesley Publishing Co., 1995 (which is incorporated herein by reference for all purposes).

As shown, server 136 includes an operating system 150 (e.g., UNIX) on which runs a relational database management system 152, a World Wide Web application 154, and a World Wide Web server 156. The software on server 136 may assume numerous configurations. For example, it may be provided on a single machine or distributed over multiple machines.

World Wide Web application 154 includes the executable code necessary for generation of database language statements (e.g., SQL statements). Generally, the executables will include embedded SQL statements. In addition, application 154 includes a configuration file 160 which contains pointers and addresses to the various software entities that comprise the server as well as the various external and internal databases which must be accessed to service user requests. Configuration file 160 also directs requests for server resources to the appropriate hardware—as may be necessary should the server be distributed over two or more separate computers.

Each of clients 138a and 138b includes a World Wide Web browser for providing a user interface to server 136. Through the Web browser, clients 138a and 138b construct search requests for retrieving data from a sequence database 144 and/or a gene expression database 146. Thus, the user will typically point and click to user interface elements such as buttons, pull down menus, scroll bars, etc. conventionally employed in graphical user interfaces. The requests so formulated with the client's Web browser are transmitted to Web application 154 which formats them to produce a query that can be employed to extract the pertinent information from sequence database 144 or gene expression database 146.

In the embodiment shown, the Web application accesses data in gene expression database 146 by first constructing a query in a database language (e.g., Sybase or Oracle SQL). The database language query is then handed to relational database management system 152 which processes the query to extract the relevant information from database 146. In the case of a request to access sequence database 144, Web application 154 directly communicates the request to that database without employing the services of database management system 152.

The procedure by which user requests are serviced is further illustrated with reference to FIG. 2B. In this embodiment, the World Wide Web server component of server 136 provides Hypertext Mark-up Language documents ("HTML pages") 164 to a client machine. At the client machine, the HTML document provides a user interface 166 which is employed by a user to formulate his or her requests for access to database 146. That request is converted by the Web application component of server 136 to a SQL query 168. That query is used by the database management system component of server 136 to access the relevant data in database 146 and provide that data to server 136 in an appropriate format. Server 136 then generates a new HTML document relaying the database information to the client as a view in user interface 166.

While the embodiment shown in FIG. 2A employs a World Wide Web server and World Wide Web browser for a communication between server 136 and clients 138a and 138b, other communications protocols will also be suitable. For example, client calls may be packaged directly as SQL statements, without reliance on Web application 154 for a conversion to SQL.

When network 130 employs a World Wide Web server and clients, it must support a TCP/IP protocol. Local networks such as this are sometimes referred to as "Intranets." An advantage of such Intranets is that they allows easy communication with public domain databases residing on the World Wide Web (e.g., the GenBank World Wide Web site). Thus, in a particular preferred embodiment of the present invention, clients 138a and 138b can directly access data (via Hypertext links for example) residing on Internet databases using a HTML interface provided by Web browsers and Web server 156.

Bare in mind that if the contents of the local databases are to remain private, a firewall 140 must preserve in confidence the contents of a sequence database 144 and a gene expression database 146.

In a preferred embodiment, the gene expression and sequence databases include a plurality of tables not directly associated with the full-length project information described above. In one specific embodiment, these tables provide information about ESTs which as noted above are short sequences (about 50–300 base pairs) of cDNA transcribed from mRNA. As noted, these EST sequences may be used to assemble or cluster with full-length sequences. An example of an EST database is the LifeSeq™ database available from Incyte Pharmaceuticals, Inc. and described in U.S. Provisional patent application No. 60/028,284, previously incorporated by reference.

In a preferred embodiment, sequence database 144 is a flat file database including separate partitions for full-length nucleotide sequences and full-length peptide (amino acid) sequences. If it contains other information such EST sequences, these may provided in a separate partition. Other approaches include partitioning the sequence data according to species such as human, primate, rodent, etc. Still further, separate partitions may be provided for sequences that have been found to be unique to the local database (i.e., sequences that did not have any hits in an external database such as GenBank).

Preferably, the information in gene expression database 146 is stored in a relational format. As mentioned, it may include tables for both full-length projects and ESTs. In Oracle™ databases, for example, the various tables are not physically separated, as there is one instance of work space with different ownership specified for different tables. In Sybase™ databases, in contrast, the tables for the full-length projects and the table for ESTs may be physically segregated into different "databases."

One specific configuration for network 130 for multiple users provides both the Gene Expression and Sequence databases on the same machine. If there is a high volume of sequence searching, it may be desirable to have a second processor of similar size and split the application across the two machines to improve response time.

A suitable dual processor server machine may be any of the following workstations: Sun—Ultra-Sparc 2™ (Sun Microsystems, Inc. of Mountain View, Calif.), SGI—Challenge L™ (Silicon Graphics, Inc. of Mountain View, Calif.), and DEC—2100A™ (Digitial Electronics Corporation of Maynard, Mass.). Multiprocessor systems (minimum of 4 processors to start) may include the following: Sun—Ultra Sparc Enterprise 4000™, SGI—Challenge XL™, and DEC—8400™. Preferably, the server machine is configured for network 130 and supports TCP/IP protocol.

Depending upon the workstation employed, the operating system may be, for example, one of the following: Sun—Sun OS 5.5 (Solaris 2 5), SGI—IRIX 5 3 (or later), or DEC—Digital UNIX 3 2D (or later).

The databases of this invention may be downloaded via a 4×4 Gb+ FWSCSI-2, Fiber Link Raid Units 2OGb+, or 4 DAT Tape Drive. A CD ROM drive may also be acceptable.

The client machine may be, for example, a Macintosh™ (Apple Computer Inc. of Cupertino, Calif.), a PC, or a Unix workstation. It should also be TCP/IP capable with a Netscape Web Browser.

The network may include a 10-base-T connection, be TCP/IP capable, and provide access to Internet for HTML hyperlinks to NCBI.

5. Model of the Gene Expression Relational Database

Turning now to FIG. 3, a block diagram is shown of a physical data model 200 for a gene expression relational database 146 in accordance with one embodiment of the present invention. Each block represents a separate relational table provided in database 146. Relationships between records in the various tables are indicated by lines between related tables, with one-to-many relationships indicated by branches. For example, each record in a table FL_Sequences 204 has a one to many relationship with the records in a table 206 labeled "FL_ProjAllSeq". In contrast, each record in the FL_Sequences table 204 has a one to one relationship with the records in a table 208 denoted "FL_ProjectSequences." Optional relationships are indicated by circles in the connecting lines.

The sequences found in the FL_Sequences table 204 represent all sequences associated in any way with a given full-length project. This includes sequences that are generated to form the project itself (i.e., those sequences used to assembly the full-length sequence) as well as sequences clustered with the representative sequence from the full-length project. The primary key of table 204 is the SequenceID for each sequence.

A table 210 named "FL_Project," in contrast, has a unique ProjectID (FL_ProjectID) as its primary key. Thus, it includes a single record for each full-length project. The attributes of records in table 210 include a representative sequence ID for the project, and a hit ID and hit type for the representative sequence. The hit ID refers to an identifier for a hit against an external database (e.g., GenBank). In a preferred embodiment, the hit ID is simply the ID used by GenBank (or other external database) to identify the sequence that has been hit. The hit type is "g" for a GenBank ID. Together the hit type and hit ID uniquely specify the external database "hit" sequence. The FL_Project table 410 also includes project Status field which may have the values "first pass", "assemblage", "5' complete", or "full-length" as described above. Finally, the FL_Project table 410 includes "Expression" and "ExpressionID" fields. These represent the expression categories in which a project might fall, for example, "Induced Expression" or "Tissue specific, cardiovascular."

In the FL-Sequences table, attributes other than the SequenceID (primary key) include a CloneID, various sequence related attributes, various BLAST related attributes (for sequences having a hit against an external database), various external hit attributes, a sort order, an amino acid flag, and a protein function hit flag. As for the CloneID, note that multiple sequences can be provided for a given clone. The SeqType field specifies whether the project sequence is full-length, expression, etc. The SeqCoverage field specifies whether the 5' coverage is complete or not. The SeqLength field specifies the sequence length in number of base pairs. The Hit_Description-Short field contains an abbreviated version of the description from the external database. The Hit_DataSource field references a specific database within GenBank, for example. Examples include GenBank rodent database (gbrod) and GenBank primate database (gbpri). The hit description field is preferably an annotated description of each hit taken from the public database. The hit description may be generated in house or simply taken from the description provided in the public database.

The Sort_Order field has a different value for each sequence type and is used by the system to determine the sort order when sequences are displayed. The AminoAcid_YN field is a flag for amino acids. When the sequence at issue is an amino acid, this field is set to "Y". Finally, the PFHit_YN field is a flag for protein function hierarchies. If a sequence has an associated protein function category, the flag is set to "Y".

A table 212 denoted "FL_NorthernAbun" and a table 214 denoted "FL_NorthernClone" include the necessary information to display the results of an electronic northern query. The fields contained in the FL_NorthernAbun table 212 include the FL-ProjectID and a LibraryID which together form the primary key for this table. In a preferred embodiment, the LibraryID specifies the library in which a full-length sequence of a project was found. Other attributes in table 212 include an abundance field specifying how many clones in the specified project occur in the specified library and the percent abundance specifies the abundance attribute divided by the total number of clones in the library.

The fields contained in the FL_NorthernClone table 214 include the project and library IDs as the primary key and a CloneID. In a preferred embodiment, an electronic Northern query is handled as follows. The user enters a ProjectID or a CloneID, and the system returns an electronic Northern results screen listing the ProjectID number or CloneID number in the header. The Northern results page also includes a listing of all libraries in which the full-length sequence associated with the selected project or clone appeared. Each entry in this list specifies the library ID, a library description, and abundance of the selected sequence within the library and a percentage abundance of that sequence within the library. Some or all of the information returned in the Northern results screen may be from outside of the project database, for instance, Incyte Pharmaceutical's LifeSeq™ database.

Tables 206 and 208 (FL_ProjAllSeq and FL_ProjectSequences, respectively) are employed to facilitate the join operations required to handle sequence information queries in which a user wishes to view those sequences associated with a particular project. Both tables 206 and 208 include only ProjectID and sequence ID fields. As explained below, a user may specify that a selected project be displayed with only those sequences required to assemble a project representative sequence or, alternatively, include the sequences employed in both the assembly procedure and the clustering procedure. If the user requests both the clustering and assembly sequences, then table 206 is employed in the join operation. In contrast, if the user requests only those sequences used to assembly the representative sequence within the project, then table 208 is employed. This is because table 208 is populated with only the representative sequence and associated sequences used to construct the representative sequence associated with the given project. In contrast, table 206 includes all sequences, employed during assembly and clustering, associated with a given project.

A table 216 denoted "FL_Project AKA" includes a "merged ProjectID" field and a ProjectID field. This table is provided to allow continuity between sequential data releases in which two projects are merged into a single project. Plus, if a user enters a ProjectID associated with a project that has been merged with another project, the system will still recognize the old ProjectID and return information associated with the merged project. Further, the user will automatically receive his or her desired information without knowing ahead of time that the desired project had merged.

A table 218 denoted "FL_ExternalHit" includes information pertaining to the "hits" against public databases. Specifically, if a sequence within the FL_Sequences table 204 matches with sufficient specificity a record in a public database such as the GenBank or Blocks databases, then the match from that public database is provided as a record in table 218. Each record in table 218 includes a hit ID, a hit type, and a hit description. The hit ID and hit type attributes together specify the primary key of this table.

A table 220 denoted "FL_PFExternalHit" includes records which tie external hits to specific protein function hierarchies. These hierarchies and their applications will be described in more detail below. The records in table 220 include the hit ID and hit type as described above, and in addition a PF_ID (protein function identifier) which uniquely specifies each category in the protein function hierarchies. Note that the relation between table 218 and 220 is a one to many relationship. This is because each unique hit from a public database (presented in table 218) may fall under multiple categories within the protein function hierarchies allowed in table 220. The primary key of table 220 includes a combination of PF_ID, hit ID, and hit type.

A table 222 denoted "FL_ProteinFunction" uniquely specifies each protein function category within the one or more hierarchies supported in this invention. The records of table 222 include a protein function identifier (PF_ID) which uniquely identifies the categories of the protein function hierarchies. This value may be displayed to users viewing protein hierarchy information. In addition, the records of table 222 include a protein function type (PF_Type) which uniquely specifies which of the various hierarchies the particular category falls under; an enzyme hierarchy, a molecular function hierarchy or a biological function hierarchy, for example. The combination of PF_ID and PF_Type form the primary key. Still further, the records of table 222 include a protein function description attribute (PF_Description) and a protein function full identifier (PF_Full_ID). The protein function description attribute includes a short textual description of the associated category. For example, non-histone chromatin proteins may be specified in the description field. The full ID may be used to internally identify the categories. Note that the relationship between the records in table 222 and those in table 220 is a one to many relationship. This is because each category within the protein function hierarchies may be represented by multiple hits from a public database.

Finally, a table 224 denoted "FL_version" includes various pieces of information regarding the software release. As shown, the record in this table includes the attributes software product (e.g., a full-length product), a software version number, and a data release month and year. This last field is necessary because a given version of a software product may have multiple data releases. In other words, the entity releasing the software (or another entity) may periodically update the data sequences and other data included in the relational database. When such updates occur, the data release month and year field of table 224 must be updated.

6. Graphical User Interface for Full-length Sequences Database

In a preferred embodiment, the invention is provided together with a suite of functions made available to users through a collection of user interface screens (e.g., HTML pages). Typically, the interface will have a main menu page from which various lines of query can be followed. Of particular relevance to the present invention is a main menu page which allows users to travel toward information regarding protein functions.

FIG. 4A presents one such main menu page 302 which may be employed in a database having a full-length sequences contained therein. As shown menu page 302 includes buttons for accessing the following lines of query: protein function (button 304), project information (button 306), Northern (button 308), expression (button 310), and sequence database (button 312).

If a user selects button 304, he or she will be presented with a list of categories from one or more protein function hierarchies. One suitable format for this information is a Protein Function Query page as shown in FIG. 5B. The user may then select one or more categories from the hierarchy (ies) to bring up those sequences in the database that meet criteria for grouping the selected categories. This line of query will be described in more detail below.

Should the user select button 306 (project information), he or she will receive a Project Information Query screen (such as shown in FIG. 4B). In a preferred embodiment, the user can enter a full-length project identifier in this query screen and the system will return a list of information about the selected project (e.g., the sequence members of the project, the project status, etc.). Alternatively, the user may enter a particular clone identifier, hit description, etc., and in turn receive a listing of all projects containing members meeting the entered criteria.

When the system determines that button 308 (an Electronic Northern analogous to a Northern Blot) has been selected, it will allow the user to investigate expression occurrence and abundance levels for a particular sequence. For example, a user may enter a project identifier in a Northern query screen. The system may then return all libraries, in decreasing percent abundance (percentage of total sequences from library that correspond to members of the identified project) that contain members of the project.

If the user should select the button 310 (Expression), the database system will allow the user to query projects by expression category. For example, expression profiles predesignated as being of special interest may include: Induced expression, regulated expression, secreted, splice variant, and the following tissue specific categories: cardiovascular, dermatologic, developmental, endocrine, gastrointestinal, hematologic, hepatic, musculoskeletal, nervous, pancreas, reproductive—female, reproductive—male, respiratory and urologic. A user may select from one to all categories in order to return information about the projects in each selected category. Other expression categories may also be designated.

The project information, Northern and expression lines of query are described in more detail in a companion patent application Ser. No. 08/811,758, filed concurrently herewith and previously incorporated by reference.

Finally, when the system determines that the user has selected button 312 (Sequence Database), it allows the user to retrieve actual amino acid and nucleotide sequences for given Sequence IDs. It also allows the user to perform sequence alignment searches (e.g., BLAST, FASTA) against various sequence databases (typically external databases), and to assemble nucleotide sequence fragments from a cluster and view how they overlap with each other.

Preferably, the user interface employed with this invention possesses similar attributes to interfaces for other sequence databases (besides a full-length projects database). Examples of other databases including similar interfaces might include (1) a general purpose short sequence database (containing for example ESTs as in the case of Incyte Pharmaceutical's LifeSeq™ database and interface), (2) a microbial genomic sequences database (such as Incyte Pharmaceutical's PathoSeq™ database and interface), and a plant genomic sequences database (such as Incyte Pharmaceutical's PhytoSeq™ database and interface). The "look and feel" of each of these databases preferably will resemble one another. For example, each might contain a commonly formatted collection of query buttons as shown as buttons 304, 306, 308, 310, and 312 in the main menu page of FIG. 4A. As a result the system may bring one of multiple available "query" screens, each commonly formatted to allow the user to formulate his or her query. Upon execution of this query, the system may present an appropriate results screen (again of common format) presenting the results of the executed query.

By providing these features as a common interface spanning multiple sequence databases, users familiar with one database interface can quickly learn to navigate through related databases. Thus, they will be able to leverage their knowledge of formulating appropriate queries and locating desired sequence information obtained from working with an initial database (e.g., the LifeSeq™ database). This is the motivation behind providing any standard. In this case, the inventors have recognized that sequence database interfaces currently available have disparate looks and feels. By standardizing the look and feel of multiple sequence databases, the inventors have brought a needed consistency to the sequence database industry.

In a preferred embodiment, the user interface facilitates project data analysis at three levels: a project level, a project sequence level, and a BLAST search level. This allow users to drill down from a high level description of the project, to the actual sequence(s) associated with project single sequence in the case of EST database), and finally to BLAST against public database.

Suitable interface screens for handling this three level drilling are depicted in FIGS. 4B–4E. In FIG. 4B, a project information query screen 324 is shown. This screen includes a menu button 326 which allows the user to select the type of search query to input. As shown in FIG. 4B, menu 326 is set to "ProjectID." While in this mode, the user is expected to enter one or more ProjectIDs in a field 328. Thereafter, if the user selects a "Search" button the system will return a Project Information Results screen as depicted in FIG. 4C listing information about the entered project (e.g., the project's status, representative sequence, hit description, etc.).

Alternatively, menu button 326 may be selected to allow a choice of "CloneID," "Hit_ID," or "Hit_Description" for example. If the user chooses CloneID, the system expects him or her to enter a desired CloneID in field 328. Each clone in the database has a unique CloneID associated therewith. Upon selection of the Search button 334, the system returns a list of projects with which the selected clone is associated (i.e., projects employing the clone as the birth clone, a member an assemblage, or a member of a cluster). This information may be displayed in a Project Information Results Screen as depicted in FIG. 4C.

Similarly, if the user chooses a Hit_ID or Hit_Description format from menu button 326, he or she will enter an appropriate ID or description in field 328. Upon selection of Search button 334, the system returns a Results screen listing projects containing sequences (as assemblages or clusters for example) that possess the chosen Hit_ID or Hit_Description.

Note that Project Information Query screen 324 includes a "Clear" button allowing users to clear a previous query from field 328. Other features of screen 324 include a "Full-Length" button 332, a "5' Complete" button 330, and a "Secreted" button 331. Selecting button 332 presents a list of projects whose status is "Full-Length" in a Project Information Results Screen. Similarly, selecting button 330 presents a list of projects whose status is "5° Complete" in a Project Information Results Screen. Selecting button 331 presents a list of projects whose category is "Secreted" (that is, projects whose proteins are secreted from the cells in which they are manufactured) in a Project Information Results screen. Of course, other such buttons may be provided to allow a user to directly access specific information in the database. Finally, Query screen 324 includes a row of buttons 338 allowing the user to directly transition to a query page for any of the subjects available through the main menu (e.g., project information, protein function, Northerns, sequence database, and expression). In addition, the user can return to the main menu by selecting a "Main Menu" button from row of buttons 338. Further, the user can receive on line help by selecting a "Help" button from row 338.

FIG. 4C presents a "Project Information Results" screen 340 which returns after a search is executed with Project Information Query screen 324. As mentioned, this screen presents information about each project identified in the search from screen 324. Thus, this screen presents "first level" information (i.e., project information) in the drilling process mentioned above. Specific presented information may include, in a record 342, a ProjectID, a project Status, a Representative SequenceID, a Hit_ID, a Hit Description, a Source (i.e., the external database in which the hit occurred), a BLAST score for the hit, and a P-Value for the hit. The last five columns present information based upon the representative sequence of the project. For example, if the project contains a 5' complete sequence as its representative sequence, then the Hit ID, Hit_Description, Source, BLAST score, and P-Value will all be based upon a hit of that 5' complete sequence against an external database.

Some of the information in record 342 is linked (e.g., via an HTML link) to other information in the database. Such information is indicated by underlining on the pertinent value. Of particular relevance to the three-tiered approach described here is a link from the ProjectID value. If a user selects this value, by double clicking on it for example, the system returns a Sequence Information Results screen such as screen 344 shown in FIG. 4D. This screen includes a list 346 of all sequences within the selected project. Thus, this screen presents the second level information which the user may review to evaluate the project's assembly for example. Note that all entries in the "ProjectID" column have the same value.

Other attributes of the records in list 346 include an assembly checkbox to select sequences for assembly, a Sequence ID, a Sequence Type (within the project), a ProjectID, a Hit-ID, a Hit_Description, a Source, a BLAST Score, and a P-Value. Some of these fields provide links as in Project Information Results screen 340.

The Sequence ID field also provides a link. By selecting a specific sequence ID, the user may enter the third tier of the analysis. Specifically, in a preferred embodiment, a Sequence Retrieval Results screen 348 is displayed. This screen displays the sequence itself in a sequence field 350. In addition, information about the sequence is provided above the actual sequence in a row 352. The user can conduct BLAST searches of the sequence against external databases by using search buttons 354.

7. The Protein Function User Interface

The gene expression relational database of this invention may employ one or more protein hierarchies such as those specified in table 222 as shown in FIG. 3. As indicated, this table provides the protein hierarchy itself as specified by attributes including a protein function ID, a protein function full ID, and a protein function description. Preferably, the protein function table includes at least one hierarchy of "biological functions" such as that presented in Heirarchy A and another hierarchy of "molecular functions" such as that presented in Hierarchy B. In addition, the protein function table preferably includes an "enzyme function" list (or "EC list") as provided by the Enzyme Commission and maintained at the Enzyme Nomenclature Database at the Swiss-Prot site maintained by the University of Geneva. However, the database need not include this specific collection of protein function hierarchies. Preferably, the organizing principle of a hierarchy will be an important aspect of gene function. For example, the biological function hierarchy may be thought of as being organized on the principle of "Why" a gene's function is important; and the molecular hierarchy on the principle of for "What" a gene's function is important. Other hierarchies might be organized on a "Where" principle, such as a hierarchy based upon the tissues, cells or subcellular locations in which proteins are expressed, or a "When" principle, such as a hierarchy based upon or temporal or developmental expression patterns.

Preferably, the molecular function hierarchy is more general than the EC list. Thus, it need not be limited to enzymes (i.e., proteins that catalyze chemical reactions). Further, a robust molecular function hierarchy need not classify enzymes based exclusively upon the substrates that they act on. In comparison to biological function hierarchies, molecular function hierarchies are more locally focused. They are focused on the direct molecular structure or action of the protein. They are less concerned with biological pathways or cascades at a cellular, tissue, or organism level. Hierarchy B provides one good example of a molecular function hierarchy.

A biological function list preferably categorizes proteins by a common end biological function or "pathway" such as oncogenesis or apoptosis. The focus is more global than the molecular function hierarchy. In a preferred embodiment, the hierarchy includes a categories at multiple levels of focus in biology. Examples of such levels include a cellular level, a tissue level, and an organism level. An example of a cellular level category is DNA repair, an example of a tissue level category is apoptosis, and an example of an organism level category is development. Hierarchy A provides a good example of a biological function hierarchy.

The hierarchies of the present invention may be employed in various ways. In a first approach, a user may specify one or more categories from a hierarchy (or hierarchies). The system will then return a list of all sequences which meet these criteria. In another approach, a user may specify one or more sequences from the database. In response, the system can return a list of all functional categories associated with the sequence(s).

While the protein function hierarchies of this invention are described in the context of a full-length sequence database, they need not be limited to any one particular database or user interface. For example, specified sequence (s) may be stored in a database containing exclusively ESTs or full-length sequences, for example. Further, the interface may allow the user to select one or more sequence for categorization by various means such as hypertext links, fields for typing in text, or lists sequences for specific selection.

Preferably, the user will be allowed to formulate searches that contain categories from orthogonal hierarchies. For example, the search may specify one category from a biological function hierarchy and another category from a molecular function hierarchy. For example, a user may wish to investigate all database sequences classified as transcription factor (molecular function) and DNA repair (biological function).

The grouping of database sequences in the various categories of the protein function hierarchy (or hierarchies) can be accomplished in various ways. Generally, the approach requires some knowledge of the particular protein associated with the sequence. In a preferred embodiment, this information is obtained by matching the database sequence against sequences in an external database which has some description of the genes in the database. Preferably, the external database is GenBank or a related database.

Other approaches to obtaining the protein function may be employed. If the sequence is an amino acid sequence, such information may be directly available from studies of the actual peptide or by predicting functions based upon the structure. If the sequence is a nucleic acid, functional information may be employed by converting a properly aligned nucleic acid sequence to an amino acid sequence.

In the physical data layout presented in FIG. 3, the hierarchy information is stored as combinations of the external hits and associated protein function categories in the PFExternalHit table 220.

Each classification in the protein function table may qualify none, one, or many sequences. Thus if an external database is employed to correlate protein functions to sequences, multiple "external hits" from external databases may be associated with a given category.

In the example hierarchies shown in Hierarchy A and B, each protein function ID may correspond to a unique protein function description. Thus, for example, protein function ID "B.2. 1.3.0" corresponds to the molecular function description "Chloride channels." In this embodiment, the ID specifies a protein function type. For example, the "B" prefix in "B.2.1.3.0" specifies that the protein function is of the molecular function type. In the specific embodiment presented here, the protein function type may be either "biological function" (as shown in Hierarchy A), "molecular function" (as shown in Hierarchy B) or "enzyme function" (from the EC list). In the examples of hierarchy A and B, the hierarchy includes three and four levels of detail, respectively. Of course, the table may include any number of levels.

A specific embodiment will now be described with reference to FIGS. 5A through 5F. If a user wishes to investigate a particular type of protein, he or she may select a desired category or categories from the biological, protein, or enzyme functional hierarchies. As a result, all external hits (and associated sequences) grouped with that classification will be displayed. These external hits may then be further evaluated for various purposes.

FIG. 5A presents a process flow 400 for a preferred user interface of this invention. The process begins at 402 and in a step 404 the system receives a selection of a particular hierarchy. For example, the system may register a user's selection of a biological, molecular, or enzymatic hierarchy. At this point, the system displays a list of the categories belonging to the selected hierarchy. See process step 406. Often the list will be too large to fit on a single screen, so the user interface may be provided with scrolling controls for the list.

Next, at a step 408, the system determines which category or categories from within the hierarchy have been selected. Typically, these are categories selected by the user from the list displayed in step 406.

In a preferred embodiment, the merge option allows users to choose a higher-level category from the Enzymatic/ Molecular/Biological Hierarchy list and get an uninterrupted list of all clones within the subcategories of that selected category. For example, if the user selects Transport (B.2.0.0.0) from the Molecular Hierarchy list, then all clones found in the Transport subcategories will be displayed as a single, uninterrupted list, in decreasing order of abundance, rather than divided into individual subheadings (such as Potassium channels and Calcium channels).

To address the possibility of a "merge," the system determines whether the user has elected to merge the categories at a step 410. Thereafter, the system determines, at a decision step 414, whether the user has selected a search button (or otherwise initiated a search).

The system allows the user to exit from the protein function query mode. The user may take this route at any time by exiting the program or selecting a screen unrelated to the protein function query. This option is depicted at a decision step 416 where the system determines whether the user has selected a link to another screen or exited the program. For purposes of illustration, this step is performed after decision step 414 is answered in the negative. Of course, this step could equally well have been depicted anywhere in the flow of process 400. For illustration, process control is shown returning to decision step 410 when step 416 is answered in the negative. If decision step 416 is answered in the affirmative (i.e., the user elected to leave the protein function query mode), the system displays the linked screen if necessary at a step 418. The process is then completed at 422.

If the user selects the search button (i.e., decision step 414 is answered in the affirmative), it is determined at a decision step 415 if the user elected a merge at step 410. If the answer is affirmative, then the system merges the parallel categories as described at a step 412, and a step 420a returns a merged list of projects (or sequences in sequence database) falling within the selected category or categories. If the decision step 415 is answered in the negative, a step 420b returns a segregated list of projects (or sequences in sequence database) falling within the selected category or categories. The process is then completed at 422.

FIG. 5B presents a screen shot of a user interface HTML page 426 provided for accepting user queries pertaining protein functions. The user selects a particular hierarchy by clicking on one of buttons 428 and 430. These buttons always represent the hierarchies that are not currently displayed in a categories field 432. In the situation illustrated in FIG. 5B, the molecular hierarchy is displayed in field 432, so buttons 428 and 430 are labeled "enzyme hierarchy" and "biological hierarchy." If a user clicks on button 428, the system receives this selection (step 404) and displays the categories of the enzyme hierarchy in field 432 (step 406). The system also automatically changes the button labels to include a button for the molecular hierarchy.

The user may select one or more categories from field 432 (with or without first scrolling) by clicking on the desired categories. The system identifies the selected categories at a step 408. The user may elect to merge subcategories as described above by selecting a merge checkbox 434.

The search may be initiated by clicking on a "Search" button 436 (step 414). The selected categories may be cleared by selecting a "Clear" button 438. A "View Hierarchy" button 440 is used to more fully display a list of the hierarchy categories in a screen 444 shown in FIG. 5C.

After the search button is selected, a "Protein Function Results Screen," such as screen 446 shown in FIG. 5D, is displayed. This screen lists one or more records 448 under category headings 450 for each of protein function categories obtained in steps 408 and 412.

The step of returning a Protein Function Results page (step 420 of FIG. 5A) may be easily implemented with a database such as database 200 shown in FIG. 3. Upon notification that the user has selected one of the categories from page 426 (FIG. 5B), the system may join the FL__PFExternalHit table 220 with FL__Project table 210 on the fields Hit__ID and Hit__Type where the Hit__ID and Hit__Type are those associated with the selected protein function category. Note that in table 210, the Hit__ID and Hit__Type are indicated as attributes representative of sequence Hit__ID and representative of sequence Hit__Type. This is because each project, while having multiple sequences, has only a single representative sequence. An appropriate view created from this join is obtained by selecting the projectID, status, representative sequence ID (RepSeqID), and the Hit__ID from the FL__Project table 210. The Hit__Description, Source, Score and P-Value fields are obtained by joining the FL__Project table to the FL__Sequences table on the RepSeqID attribute.

As shown in FIG. 5D, the records in Protein Function Results screen 446 include hypertext links to Project ID, Hit ID, Hit Description and BLAST score. Of particular interest is the link under Hit Description. As noted, the protein function hierarchies of this invention may be used to assist in categorizing a sequence or project of interest. While many possible procedures may be provided to facilitate such categorization, in a preferred embodiment the associated category or categories are returned when a user selects the Hit Description link for a record of interest. Such links are shown in the Project Information Results screen 340 (FIG. 4C) and Sequence Information Results screen 344 (FIG. 4D), as well as Protein Function Results screen 446.

A preferred process flow for allowing users to determine protein function categories associated with selected sequences is shown in FIG. 5E. A process 454 begins at 456 and in a step 458 the system displays a description (e.g., the Hit Description derived from an external database) of a sequence (or representative sequence from a project). Next, the system determines whether the user has selected the description at a step 460.

To allow for the possibility that the user is not interested in viewing categories associated with a sequence, the process flow is shown including a decision step 462 where the system determines whether the user has selected a link to another page (screen) or exited the program. This step is shown, for the sake of convenience, as being executed after the decision step 450 has been answered no. Assuming that the user has opted to not view categories (i.e., step 462 is answered no), the system displays the linked page if necessary at a step 464 and the process is completed at 476. If on the other hand, step 462 is answered in the negative, process control is shown returning to step 458 indicating that the description remains displayed.

The loop including steps 458, 460, and 462 is provided primarily for purposes of illustration. It should be understood that the invention is not limited to this arrangement (or any polling procedure) and may merely await receipt of an appropriate event from the user interface, for example.

If the user selects the description (i.e., step 460 is answered in the affirmative), the system returns a Functional Categories screen displaying the one or more protein function categories associated with the selected description. This step is depicted in block 466. Now the user can tell into which protein function categories his or her selected sequence is categorized.

The user now has the option of conducting further investigation unrelated to the protein function hierarchies or determining which other projects (or sequences) fall under one of the displayed protein function hierarchy categories. This is illustrated as follows.

After step 466, process control moves to a decision step 468 where the system determines whether the user has selected one of the displayed protein function categories. If not, the system might determine whether the user has selected a link to another screen or exited the program at a step 470. If so, process control moves to step 464 where appropriate action is taken. If not, the system continues to display the Functional Categories screen (see step 472).

Assuming that the user has selected a protein function category from the Functional Categories page, the system returns a Protein Function Results screen listing all projects (or sequences) mapped to the selected category (see step 474). The process is then concluded at 476. In this manner, the user can quickly determine which full-length sequences within the local database likely have a function related to that of the sequence with the original description (selected at step 460).

The step of returning the functional categories page and displaying the one or more appropriate protein function categories maybe easily implemented with a database such as database 200 shown in FIG. 3. For example, when the user selects a Hit__D ascription hypertext link, the system may join the tables FL__Sequences 204 and FL__PFExternalHit 220 on the attributes hit ID and hit type where the hit ID and hit type are associated with the sequence having the selected description. In addition, the FL__PFExternalHit table 220 is joined with the FL__ProteinFunction table 222 on the PF__ID field. From the resulting view, the system selects the protein function IDs and protein function descriptions from table 222. The appropriate values are then displayed in the rows shown in functional categories page 546 (FIG. 5F).

Note that the Protein Function Results page returned in step 474 is screen 446 shown in FIG. 5D. Thus, in the interface described here, a user can identify projects associated with a selected category in two ways: by selecting a Protein Function category link from the functional categories page and by selecting categories from a list in a Protein Function Query screen 426.

A Functional Categories screen 480 is shown in FIG. 5F. As shown there, records 482 are displayed for each category associated with the selected sequence. Records 482 include a category ID field and text description of the category. A heading 484 lists the Project ID which was used in the search.

8. Populating the Protein Function Tables of the Database

The PFExternalHit table 220 (FIG. 3) may be populated by a process involving a search of information in a public database to determine where in the overall classification hierarchy external hits (matches to clone sequences) should be placed. In GenBank, relevant information often resides in that database's definitional and keyword fields. The search is preferably conducted with a set of keywords designed to reliably classify the sequence in one or both of the hierarchies (based upon text contained in the public database's descriptive information fields). In some cases, the system will be unable to classify the external hit in one of the hierarchy's classes. This may be the result of an incomplete description in the public database, or a description of a function not included in the hierarchy, for example.

In a preferred embodiment, three files are generated prior to performing the process which fills the PFExternalHit table. The first file is a list of all sequences referenced in the gene expression database by virtue of having annotation information. Each of these sequences has an "external hit" which the system will attempt to place in one of the protein function categories. The second file contains specially formatted and filtered descriptive information for each external hit. In the case of GenBank sequences, this information may be found in the definition and keyword fields. The third file contains a list of keywords designed to match the information in the second file in a manner that allows classification of the associated sequence in one of the protein function categories.

The sequences represented in the second file are located as matches with sequences from the internally generated libraries. The information in the first file could simply be obtained directly from the definition and/or keyword fields of GenBank. However, this would likely provide inadequate classification in the protein function table, because many entries in GenBank are not carefully edited. Further, inconsistent nomenclature is employed in GenBank entries. Thus, before classifying GenBank descriptive information, a system should normalize or filter GenBank descriptive information. In a preferred embodiment, the present invention employs a software filter for this purpose.

One particular software filter first parses raw descriptive information regarding GenBank sequences. The parsing routing produces, for each GenBank entry considered, the sequence's GI, GenBank definition, and GenBank keywords in a consistent file format necessary for subsequent filtering. Next, a species filter may be employed to standardize all references to a particular species. For example, GenBank references to "man", "homo sapiens", "h. sapiens", "human", "homo sap.", etc. as well as misspellings of these words are all converted to a standard term such as "human." Next, a vocabulary filter may be applied to terms appearing in GenBank keyword field. This filter standardizes the technical nomenclature such as a protein or enzyme names. Thus, for example, the vocabulary filter identifies all possible variations of the term "phosphofructokinase", and converts them to a standard term. The vocabulary filter may have a second component designed to extract keywords in the definitions section of GenBank. This is necessary because some GenBank entries do not include a complete list of keywords. Apparently some researchers do not include relevant terms in the keyword field when those terms also appear in the definitions field. Finally, a manual sort may be performed to remove redundant entries, blank lines, useless words (e.g., "unknown" and "putative" where appropriate), etc. At this point, the descriptive information from GenBank is available for searching and categorizing according to a preferred embodiment of the present invention.

Referring now to FIG. 6A, a process 500 for populating a table such as PFExternalHit is illustrated. Process 500 begins at 502, and a step 504 then sets a first category, a first GI, and a first keyword. Next, a decision step 506 determines whether the current GI matches the current keyword. This is accomplished by determining whether the keyword matches the descriptive information for the current GI as that information appears in the second file. Note that each category has a collection of keywords. As will become clear below, while a given category is being considered, the keywords are evaluated in turn to determine whether they match the current GI's descriptive information (decision step 506).

Assuming that the current keyword matches the current GI (decision step 506 is answered in the affirmative), the system next determines whether there is a "specific exclusion" for the current GI/category/keyword combination, at a decision step 508. As will be explained by example below, a specific exclusion is provided by a set of specific exclusion criteria designed to filter false matches with a particular keyword.

Assuming that there is no such specific exclusion (i.e., decision step 508 is answered in the negative), the system next determines whether there is a global exclusion for the current GI/category combination at a decision step 501. This assessment is made by comparing the current GI's descriptive information (from the second file) with one or more "anti-keywords." Each of these anti-keywords is selected to uproot false classifications. For example, category 3.1.1.0, hormones, includes as an "inclusion" keyword "hormone" and the global exclusion keyword "receptor". This is to exclude those GenBank entries referring to hormone receptors.

A pre-defined collection of specific exclusion criteria and anti-keywords is provided, along with the regular keywords, for each category in the protein function list in the third file.

Assuming that decision step 510 is answered in the negative, the system assumes that it has properly categorized the current GI. At this point, the current category/GI combination is loaded to a temporary file at a process step 512.

Assuming that process step 506 is answered in the negative, a decision step 514 determines whether the current keyword is the last keyword for the current category. If not, the keyword list is incremented by one at a step 516 and process control returns to decision step 506. Assuming alternatively that decision 514 is answered in the affirmative, a decision step 518 determines whether the current GI is the last GI in the first file. If not, the GI list is incremented by one and the first keyword for the current category is selected at a process step 520. Thereafter, process control is returned to decision step 506. Assuming that decision step 518 determines that the current GI is in fact the last GI, a decision step 519 determines whether the last category has been considered. If not, a process step 520 increments the category list by one and sets the first GI and keyword. Thereafter, process control returns to decision step 506. If decision step 519 determines that the last category has been considered, process control moves to a step 528 which will be described in more detail below.

It should be apparent from the immediate preceding that the process of populating the PFExternalHit table may be performed in three nested loops. The outer most loop increments the protein function category list. The intermediate loop increments the GI list from the first file. Finally, the inner most loop increments the keyword list within a given category. All this information may be provided in the third file.

If decision step 508 is answered in a affirmative, process control transfers to decision step 514 which determines whether the current keyword is the last keyword as described above. If decision step 510 is answered in the affirmative, process control transfers to decision step 518 which determines whether the current GI is the last GI as described above.

After each new category/GI combination is added to the temporary file at process step 512, a decision step 524 determines whether the search is now complete. This search will be deemed complete if all categories/GI combinations have been evaluated. Assuming that the search is not yet complete, (i.e., decision step 524 is answered in the negative) a process step 526 sets a new category, GI, and/or keyword as appropriate. Process control then transfers to decision step 506.

Now, assuming that the search is complete as determined at step 524, the system sets a first entry in the temporary file at a step 528. Thereafter, a decision step 530 determines whether the current categorization (category/GI combination) passes scientific judgment. This evaluation is preferably made by a scientist reviewing the category/GI combination at hand. If decision step 530 is answered in the affirmative (i.e., the current categorization passes scientific judgment), a process step 532 adds the current GI/category combination to the PFExternalHit table. Then the system determines whether the current GI/category combination is the last entry in a temporary file and a decision step 534. If not, the next entry in the temporary file is considered at a step 536 and process control transfers to decision step 530.

Assuming that the current categorization does not pass scientific judgment, process control is transferred from step 530 to step 534. Ultimately, step 534 will be answered in the affirmative (i.e., the last entry in a temporary file has been evaluated). At this point, the process is completed at 540.

In one embodiment, keywords are provided for leaf level categories only. Thus, searching is initiated only when a next category is a leaf. When a next category is not a leaf, that category is simply skipped. Ultimately, a leaf level category will be encountered and keyword matching commences.

In an alternative embodiment, some or all higher level categories having a catch-all "other" subcategory (e.g., B.2.1.0.0 "Channels" and B.2.1.99.0 "Other channels"), have their own set of keywords. When such high level categories are encountered, keyword searching commences in the manner described above. However, all seemingly successful matches are stored in a temporary file. When the keywords in that high level category are exhausted, the system moves to the first leaf level category. While there, the associated leaf keywords are matched against only those GIs stored in the temporary file. Matches to leaf keywords within this file are then categorized in the current leaf level protein function. All leaf level categories, save the "other" categories, have their own set of associated keywords. After each of the normal leaf level categories have been considered, and matches from the temporary file successfully categorized, those GIs still remaining in the temporary file are placed in the "other" category.

In this alternative embodiment, the keywords provided with the high level category should be chosen to capture all potentially relevant GIs. This ensures that the pool against which the leaf level searching is conducted is sufficiently large.

As noted, a third file contains a list of keywords designed to match the information in the second file in a manner that allows classification of the associated sequence in one of the protein function categories. An example of a suitable keyword list is provided in U.S. Provisional application Ser. No. 60/028,284, previously incorporated herein by reference. The organization of the keyword list will now be described.

The keyword list provides information in the following order: category, global exclusions, keyword, and specific exclusions. The category entry in the list is simply the numerical designation of the category (e.g., B.1.1.1.0 for microfilaments). Within the GI description, the presence of a global exclusion automatically removes that GI from grouping with the current category. Global exclusions are typically provided in form "NOT keyword" or "!keyword". So if the GI description contains an "anti-keyword" associated with the category under consideration, that GI can not be grouped in the current category, regardless of a normal keyword hit. Examples global exclusion anti-keywords for the microfilaments category might include "capping", "bundling", and "kinase". It has been discovered that many GI descriptions containing "microfilaments" in addition to one of these terms should not be grouped in the microfilaments category (e.g., the GI represents a microfilament bundling or capping protein).

Inclusion keywords appear after the global exclusions in the keyword list. An example of such inclusion keyword for the microfilaments category might be "actin" at the beginning of GI description term. A GI using such term will be grouped with microfilaments unless excluded by a global or specific exclusion.

Finally, specific exclusions appear after an associated inclusion keyword in the keyword list. Note that the specific exclusions do not apply to the entire category: only to the specific inclusion keyword with which they are associated. Thus, for example, in the category HLH proteins (B.3.4.1.2) one inclusion keyword is "id" at the beginning of a word followed immediately by a non-letter. Under this criteria, the word "idea" would not be captured but the term "Id3" would be captured. Associated with this inclusion keyword is a specific exclusion for words in which "id" is preceded by a hyphen or dash "-". This specific exclusion is noted in the keyword list as "!-id". Thus, the term hlh-id would be excluded, even though "id" occurs at the beginning of a word (after "-").

Categories from the protein function hierarchies may be selected and used according to a generalized process illustrated in FIG. 6B. This may be implemented on window 432 of a Protein Function Query page 426 shown in FIG. 5. However, the following process is more specifically focused toward a general purpose sequences database—one which allows searching to be limited to specific libraries.

A process 546 begins at 548 and at a step 550, the hierarchy list from ProteinFunction table 222 is displayed in a window. At a step 552, the system determines which row(s) of the hierarchy and which library or libraries has been selected by the user. In some cases, the user may select all libraries. The selected row may be at any level in the hierarchy. If a higher level (non-leaf) level row is selected, all lower levels under the specifically selected level are also selected.

After the system has determined which row/hierarchy combination has been selected, a process step 554 formats an output line for display in a window. Next, the system determines at a step 556 whether the row under consideration (initially the row specifically selected by the user) is a leaf. As indicated, leaves are rows of the hierarchy at lowest level, such as "calcium transporters/pumps" B.2.2.3.0. (see Hierarchy B).

Assuming that the current row is a leaf, a process step 558 obtains the external hits, if any, from the PFExternalHit table 220 and displays those hits in the currently formatted line. Thus, the user sees which sequences are classified at the selected level.

After the external hit(s) have been displayed at step 558 (or after decision step 556 is answered in the negative), a decision step 560 determines whether their are any more rows of the hierarchy of level lower than the user selected row. For instance, if a user selected B.1.1.0.0 "cytoskeleton" structural proteins and the current row is B.1.1.3.0 "microtubules", then decision step 560 will be answered in the affirmative. This is because other lower levels such as B.1.1.4.0 "coat proteins" remain under the cytoskeleton category. However, if the current row is B.1.1.99.0 "other cytoskeletal proteins," decision step 560 will be answered in the negative.

Assuming that the system determines that more lower level rows remain, it then gets the next row in the hierarchy at a step 562. From there, process control transfers to step 554 where a next output line is formatted and the process proceeds as described above. This continues until, at some row, the system determines that no more lower level rows exist (step 560). At that point the process is concluded at 570.

The user now has a list of public sequences (external hits) matching the category or categories selected. From this point, the user can locate other information about the public sequences—such as which clones or clone clusters form part of a project.

9. Conclusion

Although a few specific embodiments of the present invention have been described in detail, it should be understood that the present invention may be embodied in many other specific forms without departing from the spirit or scope of the invention as recited in the claims. For example, while the gene expression databases of this invention has been described as storing nucleic acid sequences grouped as projects (including birth clones, long read sequences, full-length sequences, etc. originating from mRNA), there is in principle no reason why other sequence units can not also be employed. For example, the databases of this invention could be employed to store genomic DNA sequences.

Hierarchy A
BIOLOGICAL FUNCTION HIERARCHY

| | |
|---|---|
| C.1.0.0.0 | Cellular-level function |
| C.1.1.0.0 | Cellular metabolism |
| C.1.1.1.0 | Energy metabolism |
| C.1.1.2.0 | Nucleic acid metabolism |
| C.1.1.4.0 | Lipid metabolism |
| C.1.2.0.0 | Signal transduction |
| C.1.3.0.0 | Cell cycle |
| C.1.4.0.0 | DNA repair |
| C.1.5.0.0 | Secretory pathway |
| C.1.6.0.0 | Sub-cellular localization |
| C.1.6.1.0 | Nuclear |
| C.1.6.2.0 | Plasma membrane |
| C.1.6.3.0 | Endoplasmic reticulum |
| C.1.7.0.0 | Ligand binding |
| C.1.7.1.0 | Calcium binding |
| C.1.7.2.0 | Growth factor binding |
| C.1.7.3.0 | Steroid binding |
| C.1.7.4.0 | Nucleic acid binding |
| C.1.8.0.0 | Cell-cell interaction |
| C.2.0.0.0 | Tissue-level function |
| C.2.1.0.0 | Apoptosis |
| C.2.2.0.0 | Growth and differentiation |
| C.3.0.0.0 | Organism-level function |
| C.3.1.0.0 | Development |
| C.3.2.0.0 | Fertilization |
| C.3.3.0.0 | Immune system |
| C.3.4.0.0 | Neurotransmission |
| C.3.4.1.0 | Neurotransmitters |
| C.3.4.2.0 | Neurotransmitter receptors |
| C.3.4.99.0 | Other neurotransmission proteins |
| C.3.5.0.0 | Disease genes |
| C.3.5.1.0 | Oncogenes |
| C.3.5.2.0 | Tumor suppressors |
| C.3.5.99.0 | Other disease genes |

Hierarchy B
MOLECULAR FUNCTION HIERARCHY

| | |
|---|---|
| B.1.0.0.0. | Structural Proteins |
| B.1.1.0.0. | Cytoskeleton |
| B.1.1.1.0. | Microfilaments |
| B.1.1.2.0. | Intermediate filaments |
| B.1.1.3.0. | Microtubules |
| B.1.1.4.0. | Coat proteins |
| B.1.1.99.0. | Other cytoskeletal proteins |
| B.1.2.0.0. | Ribosome |
| B.1.2.1.0. | Small subunit |
| B.1.2.2.0. | Large subunit |
| B.1.3.0.0. | Extracellular matrix |
| B.1.4.0.0. | Chromatin |
| B.1.4.1.0. | Histone |
| B.1.4.2.0. | Non-histone |
| B.2.0.0.0. | Transport |
| B.2.1.0.0. | Channels |
| B.2.1.1.0. | Potassium channels |
| B.2.1.2.0. | Calcium channels |
| B.2.1.3.0. | Chloride channels |
| B.2.1.4.0. | Sodium channels |
| B.2.1.50.0. | Channel inhibitors |
| B.2.1.99.0. | Other channels |
| B.2.2.0.0. | Transporters/Pumps |
| B.2.2.1.0. | Anion transporters/pumps |
| B.2.2.2.0. | Proton transporters/pumps |
| B.2.2.3.0. | Calcium transporters/pumps |
| B.2.2.4.0. | Sodium transporters/pumps |
| B.2.2.5.0. | Potassium transporters/pumps |
| B.2.2.6.0. | Phosphate transporters/pumps |
| B.2.2.7.0. | Amino acid transporters/pumps |
| B.2.2.8.0. | Protein/peptide transporters/pumps |
| B.2.2.9.0. | Vitamin transporters/pumps |
| B.2.2.10.0. | Sugar transporters/pumps |
| B.2.2.11.0. | Neurotransmitter transporters/pumps |
| B.2.2.12.0. | Viral transporters/pumps |
| B.2.2.13.0. | Metal transporters/pumps |
| B.2.2.50.0. | Transport/pump inhibitors |
| B.2.2.99.0. | Other transporters/pumps |
| B.2.3.0.0. | Carrier molecules |
| B.2.3.1.0. | 02 carriers |
| B.2.3.2.0. | Lipid carriers |
| B.2.3.3.0. | Protein/peptide carriers |
| B.2.3.4.0. | Metal carriers |
| B.2.3.50.0. | Carrier inhibitors |
| B.2.3.99.0. | Other carriers |
| B.3.0.0.0. | Regulatory Proteins |
| B.3.1.0.0. | Extracellular messengers |
| B.3.1.1.0. | Hormones |
| B.3.1.2.0. | Cytokines/Immune effectors |
| B.3.1.3.0. | Growth Factors |
| B.3.1.4.0. | Neuropeptides |
| B.3.1.5.0. | Vasomediators |
| B.3.1.50.0. | Extracellular message inhibitors |
| B.3.1.99.0. | Other extracellular messengers |
| B.3.2.0.0. | Intracellular messengers |
| B.3.2.1.0. | G proteins |

-continued

| | |
|---|---|
| B.3.2.2.0. | Cyclins |
| B.3.2.3.0. | Ras related proteins |
| B.3.2.4.0. | Calcium-sequestering proteins |
| B.3.2.5.0. | Signaling kinases |
| B.3.2.5.1. | Serine/Threonine Kinases |
| B.3.2.5.2. | Tyrosine kinases |
| B.3.2.50.0. | Intracellular message inhibitors |
| B.3.2.99.0. | Other intracellular messengers |
| B.3.3.0.0. | Receptors |
| B.3.3.1.0. | G protein coupled receptors |
| B.3.3.2.0. | Serine/threonine kinase receptors |
| B.3.3.3.0. | Tyrosine kinase receptors |
| B.3.3.4.0. | Nuclear receptors |
| B.3.3.50.0. | Receptor inhibitors |
| B.3.3.99.0. | Other receptors |
| B.3.4.0.0. | DNA regulatory proteins |
| B.3.4.1.0. | Transcription factors |
| B.3.4.1.1. | Homeobox proteins |
| B.3.4.1.2. | HLH proteins |
| B.3.4.1.3. | Leucine zipper proteins |
| B.3.4.1.4. | Zinc finger proteins |
| B.3.4.1.99. | Other transcription factors |
| B.3.4.2.0. | TF-associated proteins |
| B.3.4.50.0. | Regulator inhibitors |
| B.3.4.99.0. | Other DNA-regulatory proteins |
| B.3.5.0.0. | RNA/Translation Regulatory proteins |
| B.3.5.1.0. | Translation initiation factors |
| B.3.5.2.0. | Elongation factors |
| B.3.5.3.0. | Splicing factors |
| B.3.5.50.0. | Regulator ~ inhibitors |
| B.3.5.99.0. | Other RNA regulatory proteins |
| B.3.6.0.0. | Enzyme regulators |
| B.3.6.1.0. | Enzyme cofactors |
| B.3.6.2.0. | Protease inhibitors |
| B.3.6.3.0. | Other inhibitors |
| B.3.6.50.0. | Regulator inhibitors |
| B.3.6.99.0. | Other enzyme regulators |
| B.3.7.0.0. | Cytoskeletal regulators |
| B.3.7.1.0. | Capping/Actin-sequestering proteins |
| B.3.7.2.0. | Crosslinkers/Bundling proteins |
| B.3.7.3.0. | Motor proteins |
| B.3.7.50.0. | Regulator inhibitors |
| B.3.7.99.0. | Other cytoskeletal regulatory proteins |
| B.4.0.0.0. | Molecular recognition |
| B.4.1.0.0. | Antigen recognition |
| B.4.1.1.0. | MHC |
| B.4.1.2.0. | TCR |
| B.4.1.3.0. | Ig |
| B.4.1.4.0. | Other antigen recognition proteins |
| B.4.2.0.0. | Intercellular/matrix adhesion |
| B.5.0.0.0. | Energy transducers |
| B.6.0.0.0. | Protein metabolism |
| B.6.1.0.0. | Proteases |
| B.6.1.1.0. | Metalloproteases |
| B.6.1.2.0. | Serine proteases |
| B.6.1.3.0. | Cysteine proteases |
| B.6.1.99.0. | Other proteases |
| B.6.2.0.0. | Protease inhibitors |

What is claimed is:

1. A computer system comprising:

a database containing records pertaining to a plurality of biomolecular sequences;

a first hierarchy of protein function categories into which at least some of said biomolecular sequences are grouped, said protein function categories specifying biological functions of proteins corresponding to said biomolecular sequences and said first hierarchy including (i) a first set of protein function categories specifying biological functions at a cellular level, and (ii) a second set of protein function categories specifying biological functions at a level above the cellular level; and a user interface allowing a user to selectively view information regarding said plurality of said biomolecular sequences as it relates to said first hierarchy.

2. The computer system of claim 1, wherein the biomolecular sequences include nucleic acids.

3. The computer system of claim 2, wherein the biomolecular sequences are selected from the group consisting of ESTs, full-length sequences, and combinations thereof.

4. The computer system of claim 1, wherein the biomolecular sequences include amino acid sequences.

5. The computer system of claim 1, wherein the records include descriptive information from an external database, which information correlates said biomolecular sequences to records in said external database.

6. The computer system of claim 5, wherein the external database is GenBank.

7. The computer system of claim 1, wherein the second set of protein function categories specifies biological functions at an organism level or a tissue level.

8. The computer system of claim 1, further comprising a second hierarchy of protein function categories into which at least some of said biomolecular sequences are grouped, said second hierarchy specifying at least one of (i) molecular functions of proteins corresponding to said biomolecular sequences and (ii) enzymatic functions of proteins corresponding to said biomolecular sequences.

9. The computer system of claim 8, wherein the second hierarchy is an enzyme list provided by the Enzyme Commission.

10. The computer system of claim 8, wherein the user interface allows the user to selectively view information regarding a subset of said plurality of said biomolecular sequences which subset is grouped in both a selected category from the first hierarchy and a selected category from the second hierarchy.

11. The computer system of claim 1, wherein the user interface allows the user to view biomolecular sequence records associated with a category selected from the first hierarchy.

12. The computer system of claim 1, wherein the user interface allows the user to view categories from the first hierarchy that are associated with a selected biomolecular sequence record.

13. The computer system of claim 1, wherein at least some of said biomolecular sequences are provided as part of one or more projects for obtaining full-length gene sequences from shorter sequences, and wherein the database records contain information about said one or more projects.

14. A method of using a computer system to present information pertaining to a plurality of biomolecular sequence records stored in a database, the method comprising:

displaying a list of said records or a field for entering information identifying one or more of said records;

identifying one or more of said records that a user has selected from said list or field;

matching said one or more selected records with one or more protein function categories from a first hierarchy of protein function categories into which at least some of said biomolecular sequence records are grouped; and displaying the one or more categories matching said one or more selected records, wherein said protein function categories specify biological functions of proteins corresponding to said biomolecular sequences and said first hierarchy includes (i) a first set of protein function categories specifying biological functions at a cellular level, and (ii) a second set of protein function categories specifying biological functions at a tissue level.

15. The method of claim 14, wherein biomolecular sequences include nucleic acid sequence, amino acid sequences, or both nucleic acid sequences and amino acid sequences.

16. The method of claim 14, wherein the first hierarchy includes a third set of protein function categories specifying biological functions at an organism level.

17. The method of claim 14, further comprising matching said one or more selected records with one or more protein function categories from a second hierarchy of protein function categories into which at least some of said biomolecular sequences are grouped; and displaying the one or more categories from the second hierarchy matching said one or more selected records, wherein said protein function categories from the second hierarchy specify at least one of (i) molecular functions of proteins corresponding to said biomolecular sequences and (ii) enzymatic functions of proteins corresponding to said biomolecular sequences.

18. The method of claim 14, wherein the list of records includes a field of descriptive information from an external database containing sequence records corresponding to the records in the list of records.

19. The method of claim 18, wherein the step of identifying one or more of said records includes determining that the user has selected the descriptive information for the one or more records.

20. The method of claim 14, wherein at least some of said biomolecular sequences are provided as part of one or more projects for obtaining full-length gene sequences from shorter sequences, and wherein the database records contain information about said one or more projects.

21. A method of using a computer system to present information pertaining to a plurality of biomolecular sequence records stored in a database, the method comprising:

displaying a list of one or more protein biological function categories from a first hierarchy of protein biological function categories into which at least some of said biomolecular sequence records are grouped identifying one or more of said protein biological function categories that a user has selected from said list;

matching said one or more selected protein biological function categories with one or more biomolecular sequence records which are grouped in the selected protein biological function categories; and displaying the one or more sequence records matching said one or more selected protein biological function categories, wherein said protein biological function categories specify biological functions of proteins corresponding to said biomolecular sequences and said first hierarchy includes (i) a first set of protein biological function categories specifying biological functions at a cellular level, and (ii) a second set of protein biological function categories specifying biological functions at a tissue level.

22. The method of claim 21, wherein biomolecular sequences include nucleic acid sequence, amino acid sequences, or both nucleic acid sequences and amino acid sequences.

23. The method of claim 21, wherein the first hierarchy includes a third set of protein biological function categories specifying biological functions at an organism level.

24. The method of claim 21, further comprising displaying a second list of one or more protein molecular function categories from a second hierarchy of protein function categories into which at least some of said biomolecular sequence records are grouped identifying one or more of said protein molecular function categories that a user has selected from said second list;

matching said one or more selected protein molecular function categories with one or more biomolecular sequence records which are grouped with in selected protein molecular function categories; and displaying the one or more sequence records matching both the one or more selected protein biological function categories and the one or more protein molecular function categories, wherein said protein molecular function categories from the second hierarchy specify at least one of (i) general molecular functions of proteins corresponding to said biomolecular sequences and (ii) enzymatic functions of proteins corresponding to said biomolecular sequences.

25. The method of claim 21, further comprising determining that the user has elected to merge the selected protein biological function categories with other categories from the hierarchy, which other categories are related to the selected protein biological function categories; and performing said step of matching with both said other categories and said selected protein biological function categories.

26. The method of claim 21, wherein at least some of said biomolecular sequences are provided as part of one or more projects for obtaining full-length gene sequences from shorter sequences, and wherein the database records contain information about said one or more projects.

27. A database system having a plurality of internal records, the database comprising:

a plurality of sequence records specifying biomolecular sequences, at least some of said records referencing hits to an external database, which hits specify genes having sequences that at least partially match those of the biomolecular sequences a plurality of external hit records specifying said hits to said external database, at least some of said records referencing protein function hierarchy categories which specify at least one of biological functions of proteins or molecular functions of proteins.

28. The database of claim 27, wherein at least some of said plurality of sequence records reference biomolecular sequences belonging to one or more projects for obtaining full-length gene sequences from shorter sequence.

29. The database of claim 28, wherein the sequence records specify a sequence type which characterized the sequence according to its role in a project.

30. The database of claim 29, wherein the sequence type can be at least (i) a full-length sequence corresponding to a complete gene sequence, (ii) a 5' complete sequence containing a sequence to the 5' terminus of a gene, and (iii) a first pass sequence containing the first sequence information provided to the project.

31. The database of claim 27, wherein the external database is GenBank.

32. The database of claim 27, wherein the sequence records include descriptive information derived from said external database and pertaining to said hit.

33. The database of claim 27, wherein the biomolecular records specified by the sequence records can be amino acid sequences or nucleic acid sequences.

34. The database of claim 27, wherein the protein function hierarchy includes
   (i) a first set of protein function categories specifying biological functions at a cellular level, and
   (ii) a second set of protein function categories specifying biological functions at a level above the cellular level.

35. In an internal database, a method of using a computer system to automatically categorize biomolecular sequence records into protein function categories, the method comprising the steps of:
   (a) receiving descriptive information about a biomolecular sequence in the internal database from a record in an external database, which record pertains to a gene having a sequence that at least partially matches that of the biomolecular sequence;
   (b) determining whether the descriptive information contains one or more terms matching one or more keywords associated with a first protein function category, the keywords being terms consistent with a classification in the first protein function category;
   (c) when at least one keyword is found to match a term in the descriptive information, determining whether the descriptive information contains a term matching one or more anti-keywords associated with the first protein function category, the anti-keywords being terms inconsistent with a classification in the first protein function category;
   (d) grouping said biomolecular sequence in the first protein function category when the descriptive information contains a term matching a keyword but contains no term matching an anti-keyword.

36. The method of claim 35, further comprising a step of BLASTing the biomolecular sequence against genes in the external database to identify the record in an external database which pertains to a gene having a sequence that at least partially matches that of the biomolecular sequence.

37. The method of claim 35, wherein the external database is GenBank.

38. The method of claim 37, wherein the descriptive information is obtained from a definition section of the record in an external database, a keyword section of the record in the external database, or a combination of the definition section and the keyword section.

39. The method of claim 35, further comprising a step of filtering said descriptive information prior to step (a) to standardize terminology.

40. The method of claim 35, wherein step (c) includes the following steps:
   determining whether the descriptive information contains a term matching one or more global anti-keywords associated with the first protein function category; and
   determining whether the descriptive information contains a term matching one or more local anti-keywords associated with the first protein function category, each local anti-keyword being used only in association with a specified keyword.

41. The method of claim 35, wherein steps (b) through (d) are repeated but with a second protein function category substituted for said first protein function category.

42. A computer readable medium including program instructions for performing the following steps:
   (a) receiving descriptive information about a biomolecular sequence in the internal database from a record in an external database, which record pertains to a gene having a sequence that at least partially matches that of the biomolecular sequence;
   (b) determining whether the descriptive information contains one or more terms matching one or more keywords associated with a first protein function category, the keywords being terms consistent with a classification in the first protein function category;
   (c) when at least one keyword is found to match a term in the descriptive information, determining whether the descriptive information contains a term matching one or more anti-keywords associated with the first protein function category, the anti-keywords being terms inconsistent with a classification in the first protein function category;
   (d) grouping said biomolecular sequence in the first protein function category when the descriptive information contains a term matching a keyword but contains no term matching an anti-keyword.

43. The computer readable medium of claim 42, further comprising program instructions for performing a step of filtering said descriptive information prior to step (a) to standardize terminology.

44. The computer readable medium of claim 42, wherein the program instructions for performing step(c) include instructions for
   determining whether the descriptive information contains a term matching one or more global anti-keywords associated with the first protein function category; and
   determining whether the descriptive information contains a term matching one or more local anti-keywords associated with the first protein function category, each local anti-keyword being used only in association with a specified keyword.

45. The computer readable medium of claim 42, further comprising program instructions for repeating steps (b) through (d) with a second protein function category substituted for said first protein function category.

* * * * *

UNITED STATES PATENT AND TRADEMARK OFFICE
CERTIFICATE OF CORRECTION

PATENT NO. : 6,023,659  
DATED : February 8, 2000  
INVENTOR(S) : Jeffrey J. Seilhammer, Ingrid E. Akerblom, Christina M. Altus, Tod M. Klingler, Frank Russo, Janice Au-Young, Jennifer L. Hillman, and Timothy J. Maslyn Page 1 of 1

It is certified that error appears in the above-identified patent and that said Letters Patent is hereby corrected as shown below:

Column 17,  
Line 4, please replace "FL –Sequences" with -- FL_Sequences --.  
Line 15, please replace "Hit_Description-Short" with -- Hit_Description_Short --.  
Line 37, please replace "FL-ProjectID" with -- FL_ProjectID --.

Column 20,  
Line 56, please replace "single sequence in the case of EST database)" with -- (single sequence in the case of EST database) --.

Column 21,  
Line 29, please replace "5° Complete" with -- "5'Complete" --.

Column 22,  
Line 10, please replace "Hit-ID" with -- Hit_ID --.

Column 26,  
Line 52, please replace "Hit_D ascription" with -- Hit_Description --.

Column 30,  
Line 52, please replace "FIG. 5" with -- FIG. 5B. --.

Signed and Sealed this

Eleventh Day of September, 2001

*Attest:*

Nicholas P. Godici

NICHOLAS P. GODICI  
*Attesting Officer*  *Acting Director of the United States Patent and Trademark Office*